US008017350B2

(12) United States Patent
Mueller et al.

(10) Patent No.: US 8,017,350 B2
(45) Date of Patent: Sep. 13, 2011

(54) GLIMEPIRIDE- AND INSULIN-INDUCED GLYCOSYLPHOSPHATIDYLINOSITOL-SPECIFIC PHOSPHOLIPASE C REGULATION

(75) Inventors: Guenter Mueller, Sulzbach (DE); Wendelin Frick, Hunstetten-Beuerbach (DE); Rudolf Schneider, Niedernhausen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 80 days.

(21) Appl. No.: 11/464,245

(22) Filed: Aug. 14, 2006

(65) Prior Publication Data

US 2007/0111263 A1     May 17, 2007

Related U.S. Application Data

(63) Continuation of application No. PCT/EP2005/001553, filed on Feb. 16, 2005.

(30) Foreign Application Priority Data

Feb. 20, 2004   (EP) .................................... 04003897

(51) Int. Cl.
  *C12Q 1/00*    (2006.01)
  *C12Q 1/34*    (2006.01)
(52) U.S. Cl. ................... 435/19; 435/18; 435/4
(58) Field of Classification Search .................. None
  See application file for complete search history.

(56) References Cited

OTHER PUBLICATIONS

Muller, G.. The Molecular Mechanism of the Insulin-Mimetic/Sensitizing Activity of the Antidiabetic Sulfonylurea Drug Amaryl; Molecular Medicine, vol. 6, No. 11 (2000) pp. 907-933.*
Cremlyn, R., et. al., Derivatives of Cyclohexane-1,2-Diol-Phosphoro-Chloridate and 1-Chlor-4,5-Benz-2,6-Dioxaphos-Phorinanone-(3) 1-Oxide, Phosphorus and Sulfur and the Related Elements, vol. 10, pp. 333-338 (1981).
Muller, G., et. al., Characterization of the Molecular Mode of Action of the Sulfonylurea, Glimepiride, at Adipocytes, Hormone and Metabolic Research vol. 28, No. 9 (1996) pp. 469-487.
Muller, G., et. al., Cholesterol Depletion Blocks Redistribution of Lipid Components and Insulin-Mimetic Signaling by Glimepiride and Phosphoinositolglycans in Rat Adipocytes, Molecular Medicine vol. 8, No. 3 pp. 120-136 (2002).
Muller, G., et. al., Dynamics of Plasma Membrane Microdomains and Cross-Talk to the Insulin Signalling Cascade, FEBS Letters, Elsevier Science Publishers, vol. 531, No. 1 pp. 81-87 (2002).
Muller, G., et. al., Insulin-Mimetic Signaling by the Sulfonylurea Glimepiride and Phosphoinositolglycans Involves Distinct Mechanisms for Redistribution of Lipid Raft Components, Biochemistry, (2001) vol. 40, pp. 14603-14620.
Muller, G., et. al., Interaction of Phosphatidylinositolglycan(-Peptides) with Plasma Membrane Lipid Rafts Triggers Insulin-Mimetic Signaling in Rat Adipocytes, Archives of Biochemistry and Biophysics vol. 408, (2002) pp. 7-16.
Muller, G., et. al., Regulation of Lipid Raft Proteins by Glimepiride- and Insulin-Induced Glycosylphospatidylinositol-Specific Phospholipase C in Rat Adipocytes, Biochemical Pharmacology vol. 69, No. 5 (2005) pp. 761-780.
Muller, G., et. al., Stimulation of a Glycosyl-Phosphatidylinositol-Specific Phospholipase by Insulin and the Sulfonylurea, Glimepiride, in Rat Adipocytes Depends on Increased Glucose Transport, The Journal of Cell Biology (1994) vol. 126, No. 5, pp. 1267-1276.
Muller, G.A., et. al., The Insulin- and Sulfonylurea-Inducible Glycosylphospatidylinositol-Specific Phospholipase C Controls the Localization and Activity of Signaling Proteins in Lipid Raft Domains of Adipocytes in Differential Fashion, Signal Transduction vol. 3, No. 3-4, (2003) abstract.
Morris et al., Inhibition of GPI Phospholipase C from Trypanosoma brucei by Fluoro-Inositol Dodecylphosphonates, Biochemical and Biophysical Research Communications, vol. 244, 1998, pp. 873-876.

* cited by examiner

*Primary Examiner* — Rebecca Prouty
*Assistant Examiner* — Paul Martin
(74) *Attorney, Agent, or Firm* — J. Darrell Fontenot

(57) ABSTRACT

The present invention relates to a method for identification of a chemical compound which modulates the activity of mammalian GPI-PLC wherein
a] a mammalian cell is incubated with glimepiride;
b] hcDIGs of the cells of a] are prepared;
c] the hcDIGs from b] are incubated with a chemical compound;
d] the activity of the GPI-PLC from the hcDIGs of c] is determined.

11 Claims, 10 Drawing Sheets

GLIMEPIRIDE- AND INSULIN-INDUCED GLYCOSYLPHOSPHATIDYLINOSITOL-SPECIFIC PHOSPHOLIPASE C REGULATION

CROSS-REFERENCE TO RELATED APPLICATIONS

This application is a continuation of PCT/EP2005/001533, filed 16 Feb. 2005, which claims priority from EP Patent Application 04003897.8, filed 20 Feb. 2004.

SUMMARY OF THE INVENTION

The present invention relates to different methods for modulation of the activity of a mammalian GPI-PLC (Glycosyl-Phosphatidyl-Inositol specific Phospholipase C).

BACKGROUND OF THE INVENTION

The synthesis of inhibitor GPI2350 specific for the mammalian plasma membrane GPI-PLC was based upon the background knowledge about the (crystal) structure, substrate requirements, GPI recognition and cleavage mechanisms of bacterial and trypanosomal (G)PI-PLC as well as on inhibitors described for them so far. For trypanosomal GPI-PLC, GPI and PI are efficient and poor substrates, respectively, whereas the opposite is true for the bacterial PI-PLC. The latter has a region of protein sequence similarity to trypanosomal GPI-PLC of 80 residues ("Kuppe et al. (1989) J. Bacteriol. 171: 6077-6083"). For analysis of GPI recognition, the three-dimensional structure of PI-PLC from *B. cereus* has recently been determined at 2.2 Å resolution in complex with glucosaminyl(α1→6)-myo-inositol (GMI) and revealed the myo-inositol moiety of GMI occupying the same position as free myo-inositol, whereas the glucosamine moiety lying exposed to solvent at the entrance of the catalytic site (in "Heinz et al., (1995) EMBO J. 14: 3855-3863" and "Heinz et al., (1996) Biochemistry 35: 9496-9504). The residual portion of the core tetrasaccharide has little contact with the PI-PLC, which may explain the remarkable structural diversity of the core glycan within GPI anchors accepted. Taken together, current experimental data indicate that the catalytic mechanisms of cleavage of PI and GPI by bacterial PI-PLC as well as of GPI by trypanosomal GPI-PLC are all similar. However, it was not-known whether this is true for the adipocyte plasma membrane GPI-PLC, considering the failure of mammalian PI-PLC generating the second messenger, inositol-trisphosphate, to accept GPI anchors and of bacterial PI-PLC to cleave phosphorylated PI.

Substrate requirements of bacterial and trypanosomal (G)PI-PLC have been examined previously with PI analogs and GMI derivatives. Catalysis requires a free OH-group at the inositol-2 position. In studies using myristate-containing VSG from *T. brucei*, (G)PI-PLC was blocked competitively by 2-deoxy-inositol analogs of GMI, indicating that the inositol-2-OH is dispensable for substrate recognition, albeit required for catalysis. In addition, substrate recognition requires a charged phosphoryl group (i.e. phosphonate or phosphodiester) at the inositol-1 position ("Morris, J. C., et al., (1996) J. Biol. Chem. 271: 15468-15477"). Thus, the OH-groups at both the inositol-1 and inositol-2-positions are involved in catalysis, yet only the phosphoryl group appears to be needed for substrate recognition. Interestingly, glucosamine (α1→6)-inositol-1,2-cyclic phosphate turned out to be a better inhibitor than GMI-1-phosphate for trypanosomal GPI-PLC, but not the bacterial PI-PLC, indicating that the cyclic version may act as a product analog for the former.

Furthermore, phosphonate derivatives of GMI-1-phosphate were found to be more potent inhibitors, most likely because they are non-cleavable substrate analogs. These data fit to the proposed two-step mechanism for bacterial PI-PLC action with PI first being cleaved to produce a cyclic inositol-1,2-phosphate (cIP) structure which is then hydrolyzed to inositol-1-phosphate. Interestingly, a cIP structure can be immunologically identified as so-called cross-reacting determinant in trypanosomal VSG upon exposure to GPI-PLC from *T. brucei* indicating operation of the first (cyclization) but not of the second step (decyclization) during trypanosomal GPI-PLC catalysis. The requirement for transient or stable cIP formation is consistent with the finding that GPI anchors with their inositol residue palmitoylated at the 1- or 2-position, such as that of human erythrocyte AChE, resist phospholipase cleavage.

GMI-1-dodecylphosphonate turned out to be considerably more inhibitory than the corresponding hexyl derivative for the trypanosomal GPI-PLC which is also membrane-associated ("Morris, J. C. et al. (1995) J. Biol. Chem. 270: 2517-2524"). Interestingly, it has been found that, in the absence of carbohydrate substituents (i.e. glucosamine) on the inositol, non-cleavable analogs of inositol-1-phosphate, as exemplified by myo-inositol-1-O-dodecylphosphate, inhibit the trypanosomal GPI-PLC. The efficacy of this type of inhibitor was considerably increased upon substitution of the 2-position of 2-deoxy-inositol-1-O-dodecylphosphonates with 2-fluoro substitutions competitively inhibiting trypanosomal GPI-PLC with $IC_{50}$ of 10-90 μM ("Morris, J. C. et al., (1996) J. Biol. Chem. 271: 15468-15477"). The most potent inhibitors of GPI-PLC reported so far have both a fluoro group at the 2-position and a dodecyl-phosphonate at the 1-position of 2-deoxy-inositol being at least 5-fold more inhibitory than myo-inositol-1-O-dodecyl-phosphonic acid (Morris, J. C. et al. (1998) Biochem. Biophys. Res. Commun. 244: 873-867"). Interestingly, differential inhibition of (G)PI-PLC from *B. cereus* and *T. brucei* by some of these compounds argues that the two enzymes represent mechanistic subclasses of (G)PI-PLC.

Unfortunately, analogous data are not yet available for mammalian GPI-PLC. Surprisingly, the newly synthesized myo-inositol-1,2-cyclo-dodecylphosphonic acid (GPI-2350) turned out to be a potent inhibitor of bacterial as well as adipocyte GPI-PLC.

The initial observation that alkaline phosphatase (aP) was released from the membrane bilayer by a bacterial phosphatidylinositol-specific phospholipase C (PI-PLC) led to the identification of another type of membrane attachment for proteins involving the covalent coupling to a glycosylphosphatidylinositol (GPI) lipid.

The first complete structure of a GPI anchor was elucidated for the variant surface glycoprotein (VSG) from *Trypanosome brucei*.

The core tetrasaccharide consists of three mannose residues and a non-acetylated glucosamine, one end of which is amide-linked to the protein moiety via a phosphoethanolamine bridge and the other end of which is glycosidically linked to the 6-hydroxyl group of phosphatidylinositol (PI). PI is cleaved by (G)PI-specific phospholipases of specificity C and D ([G]PI-PLC/D) releasing diacylglycerol and phosphatidic acid, respectively, and leaving a terminal (phospho) inositolglycan (PIG) structure at the protein moiety.

Since then, bacterial PI-PLC of various origin have been commonly used to detect GPI-anchored proteins (GPI-proteins).

Lipolytic release of the protective surface coat consisting of GPI-anchored VSG by GPI-PLC is assumed to be required for *T. brucei* to achieve antigenic variation in order to escape the immune system of the host.

Since most mammalian cells and tissues express GPI-proteins, the majority of them with their GPI anchor embedded in the outer leaflet of the plasma membrane, endogenous (G)PI/PI-PLC/D may control the specific down-regulation of their cell surface expression and simultaneously the increase of the soluble protein moiety in the circulation.

Soluble forms of GPI-proteins have been detected circulating within the blood stream, such as 5-nucleotidase (5'-Nuc), Thy-1, alkaline Phosphatase (aP), and CD16 receptors. GPI-PLC could be also identified in human neutrophils, bovine brain, rat intestine and a human carcinoma cell line. GPI-PLC from rat liver has been purified to homogeneity. An endogenous GPI-PLC has been described as having the capability of releasing renal dipeptidase from porcine maximal tubules. However, elucidation of a GPI-PLC structure or gene is still missing. Whereas the mammalian GPI-PLC is membrane associated, the mammalian GPI-PLD can be recovered from all types of tissue material of different species (human, rat, bovine) as well as organs (placenta, brain, liver, serum).

The main role of GPI-PLD is probably the degradation of the GPI anchor of GPI proteins after endocytosis and trafficking to lysosomes. Mammalian tissues harbor two distinct GPI-PLD, being active in serum and at the cell surface with different functionality.

Some of the GPI-proteins, such as 5'-Nuc and aP in yeast and rodent adipocytes, do not seem to be released as soluble versions from the cell surface upon lipolytic cleavage of their GPI anchors by a GPI-PLC, both in vitro and in vivo.

Additional mild salt and/or trypsin cleavage is required for recovery of the protein moieties of some lipolytically cleaved GPI-proteins in the soluble fraction/medium after separation from the particulate fraction/cells—indicative of the existence of a receptor protein.

In these cases, the activity of GPI-PLC does not affect the localization or topology of GPI-proteins, but does, instead, modify their functional (catalytic/binding) characteristics in the course of their conversion from the amphiphilic into the hydrophilic version. The presence of an intact GPI anchor affects the conformation and behavior of the protein moiety attached to it.

In case of 5'-Nuc and Gce1, the catalytic and binding efficiency was increased in the lipolytically cleaved GPI-protein when compared to the intact form embedded in the membrane or reconstituted into detergent micelles or liposomes.

GPI-PL is up-regulated in eucaryotes by nutritional signals, as, e.g., glucose in yeast, where lipolytic processing of GPI-proteins seems to play a role during biogenesis of the cell wall, and by glucose as well as certain hormones, growth factors and drugs (e.g. insulin, glimepiride) in rodent adipocytes, myocytes and human endothelial cells.

Glimepiride, an antidiabetic drug, lowers blood glucose predominantly by stimulating the insulin release from pancreatic cells and, additionally, but to a minor degree, by mimicking metabolic insulin action in peripheral tissues, such as activation of glucose transport in muscle cells and inhibition of lipolysis in adipocytes.

The blood glucose-lowering effect of the sulfonylurea, glimepiride, is partly caused by stimulation of non-oxidative glucose metabolism in adipose and muscle cells via insulin receptor-independent activation of the IRS-PI3K pathway. In isolated rat adipocytes, the molecular mechanism of glimepiride action has been demonstrated to involve the redistribution and concomitant activation of lipid raft-associated signaling components, such as the acylated non-receptor tyrosine kinase, $pp^{59Lyn}$, and some GPI-proteins, as well as the stimulation of a plasma membrane glycosylphosphatidylinositol-specific GPI-PLC, which is also moderately activated by insulin.

Glimepiride is a sulphonylurea agent that stimulates insulin release from pancreatic-β-cells and may act via extrapancreatic mechanisms. It is administered once daily to patients with type 2 (non-insulin-dependent) diabetes mellitus in whom glycaemia is not controlled by diet and exercise alone, and may be combined with insulin in patients with secondary sulphonylurea failure.

The greatest blood glucose lowering effects of glimepiride occur in the first 4 hours after the dose. Glimepiride has fewer and less severe effects on cardiovascular variables than glibenclamide (glyburide). Pharmacokinetics are mainly unaltered in elderly patients or those with renal or liver disease. Few drug interactions with glimepiride have been documented.

In patients with type-2 diabetes, glimepiride has an effective dosage range of 0.5 to 8 mg/day, although there is little difference in efficacy between dosages of 4 and 8 mg/day. Glimepiride was similar in efficacy to glibenclamide and glipizide in 1-year studies. However, glimepiride appears to reduce blood glucose more rapidly than glipizide over the first few weeks of treatment. Glimepiride and gliclazide were compared in patients with good glycaemic control at baseline in a 14-week study that noted no differences between their effects. Glimepiride plus insulin was as effective as insulin plus placebo in helping patients with secondary sulphonylurea failure to reach a fasting blood glucose target level of ≦7.8 mmol/L, although lower insulin dosages and more rapid effects on glycaemia were seen with glimepiride.

Although glimepiride monotherapy was generally well tolerated, hypoglycaemia occurred in 10 to 20% of patients treated for ≦1 year and ≦50% of patients receiving concomitant insulin for 6 months. Pooled clinical trial data suggest that glimepiride may have a lower incidence of hypoglycaemia than glibenclamide, particularly in the first month of treatment. Dosage is usually started at 1 mg/day, titrated to glycaemic control at 1- to 2-week intervals to a usual dosage range of 1 to 4 mg/day (maximum 6 mg/day in the UK or 8 mg/day in the US).

Glimepiride lowers glucose predominantly by stimulation of insulin release from pancreatic β-cells and, to a minor degree, by mimicking metabolic insulin action in peripheral tissues, such as activation of glucose transport in muscle cells and inhibition of lipolysis in adipocytes.

Glimepiride has been demonstrated to potently induce the amphiphilic-to-hydrophilic conversion of a subset of GPI-proteins, such as 5'-Nuc, aP, and Gce1, by activation of a GPI-PLC upon treatment of primary or cultured rodent adipocytes with pharmacological concentrations.

The inositol derivative, GPI-2350, which is disclosed the first time in this invention, inhibits bacterial, trypanosome and serum GPI-PLC and GPI-PLD with high potency ($IC_{50}$=0.2-10 μM) and selectivity. GPI-2350 almost completely down regulates the GPI-PLC in intact rat adipocytes. Whereas GPI-PLC plays no role in metabolic insulin signaling, the activation of GPI-PLC is indispensable for the insulin-mimetic effects of glimepiride via the insulin receptor-independent cross-talk from detergent insoluble glycolipid-enriched lipid raft domains (DIGs) to the insulin receptor substrate-1 (IRS-1).

DIGs, which are expressed in high number in the plasma membrane of many terminally differentiated cells, such as adipocytes, are special membrane microdomains which serve as platform for membrane-mediated biological processes, including signal transduction and trafficking and sorting of proteins and lipids. They are enriched in cholesterol and (glyco)sphingolipids in the exoplasmic leaflet and in phospholipids with saturated acyl chains and cholesterol in the inner leaflet, forming a liquid-ordered phase within the bilayer. DIGs are characterized by insolubility in 1% Triton X-100 in the cold and low buoyant density upon sucrose gradient centrifugation. Based on these criteria, certain GPI-anchored, acylated and transmembrane signaling proteins have been found to be enriched in DIGs vs. non-DIG areas of the plasma membrane. Furthermore, DIGs of higher (hcDIGs) and lower cholesterol (lcDIGs) content can be distinguished from one another on the basis of their lower and higher buoyant density, respectively.

The stimulus-dependent redistribution of certain GPI-anchored as well as acylated signaling proteins from hcDIGs to lcDIGs was blocked by GPI-2350.

GPI-2350 reduced the basal and glimepiride/insulin-induced lipolytic release of GPI-proteins, such as Gce1 and 5'-Nuc, from intact rat adipocytes by lipid raft-associated GPI-PLC ($IC_{50}$=5-10 μM). Inhibition of the GPI-PLC by GPI-2350 (50 μM) led to almost complete blockade of (i) the dissociation from caveolin of $pp59^{Lyn}$ and Gce1, (ii) their redistribution from hcDIGs to lcDIGs, (iii) tyrosine phosphorylation of $pp59^{Lyn}$ and IRS-1, (iv) stimulation of glucose transport and (v) inhibition of lipolysis in response to glimepiride.

Insulin activation of the GPI-PLC had a moderate effect on lipid raft distribution; and its minor role, if any, in metabolic insulin signaling was demonstrated in the presence of GPI-2350 only, since it (e.g. tyrosine phosphorylation of IRS-1 and inhibition of lipolysis) was only marginally reduced.

Lipolytically cleaved GPI-proteins generated by the glimepiride-induced GPI-PLC remain associated with hcDIGs rather than redistribute to lcDIGs, as do their uncleaved amphiphilic versions as well as $pp59^{Lyn}$.

The cross-talk of glimepiride to the insulin signaling cascade via IRS tyrosine phosphorylation by redistributed and activated $pp59^{Lyn}$ in rat adipocytes requires activation of the hcDIGs-associated GPI-PLC.

DETAILED DESCRIPTION OF THE INVENTION

The present invention relates to a method for identification of a chemical compound which modulates the activity of mammalian GPI-PLC wherein
a] mammalian cells are incubated with glimepiride;
b] hcDIGs of the cells from step a] are prepared;
c] the hcDIGs from step b] are incubated with a chemical compound; and
d] the activity of the GPI-PLC from the hcDIGs produced by step c] is determined.

The mammalian cells used in step a] of the foregoing method are usually cells of a rodent or a dog. The rodent is e.g. a mouse, rat, or guinea pig. The method pertains also to the cell of a human, or an anthropoid such as, e.g. a chimpanzee, gorilla or the like. Such cells are e.g. pancreatic cells, muscle cells, liver cells, kidney cells, brain cells or adipocytes. The mammalian cells can be provided as well by a cell culture. For taking, graving, harvesting and processing of cells routine techniques are used (e.g. Current Protocols in Cell Biology; John Wiley & Sons; 0-471-24108-3-Looseleaf; 0-471-24105-9-CD-ROM).

Determining the activity of the GPI-PLC from the hcDIGs according to step c] of the method of the invention is performed by measuring the dissociation of $pp59^{Lyn}$ from the hcDIGs, or by measuring the redistribution of $pp59^{Lyn}$ and/or Gce1 from hcDIGs to lcDIGs, or by measuring the change of phosphorylation of $pp59^{Lyn}$ and/or IRS-1 or by measuring the stimulation of glucose transport and/or the inhibition of lipolysis.

The invention pertains further to a chemical compound which can be identified by a method of the invention as disclosed above. Such a compound is e.g. a compound having the formula I, or a derivative thereof as disclosed herein.

The invention relates also to compounds of formula I

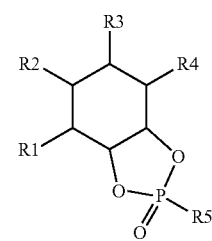

wherein $R_1$, $R_2$, $R_3$ and $R_4$ are, independently from each other, selected from H, OH and F; and $R_5$ is $(C_1-C_{20})$-alkyl or $(C_2-C_{20})$-alkenyl, in all their stereoisomeric forms, and mixtures thereof in all ratios, and their physiologically tolerable salts.

The invention pertains also to a compound of the formula I as mentioned before, wherein any two of R1, R2, R3, and R4 are, independently from each other, F.

The invention pertains also to a compound of the formula I as mentioned before wherein each of $R_1$, $R_2$, $R_3$ and $R_4$ is OH.

The invention pertains also to a compound of the formula I as mentioned before wherein the $R_5$ is $C_{1-2}$-alkyl.

Such a compound of the invention has, e.g., the following formula, including all stereoisomeric forms thereof:

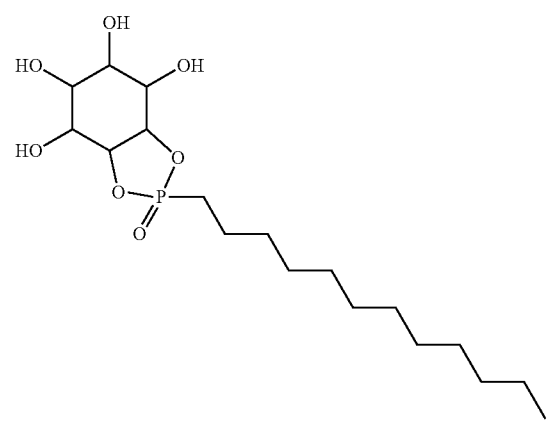

Or such a compound of the invention has, e.g., the following formula:

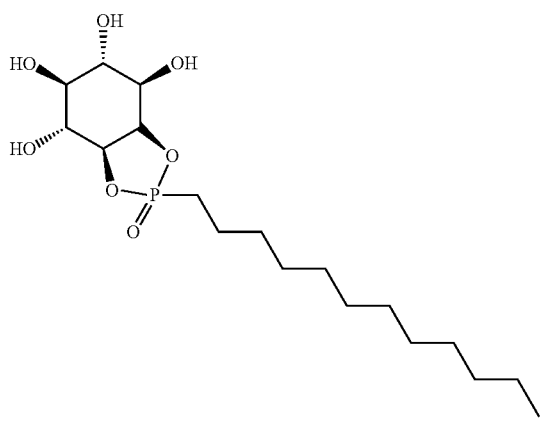

Such a compound of the invention could, e.g., be denominated as myo-inositol-1,2-cyclo-dodecylphosphonic acid, including all stereoisomeric forms thereof. In the context of this invention, the term $(C_1\text{-}C_{20})$-alkyl shall pertain to all linear or branched compounds of all stereoisomeric conformations of methyl, ethyl, propyl, butyl, pentyl, hexyl, heptyl, octyl, nonyl, decyl, undecyl, dodecyl, tridecyl, tetradecyl, pentadecyl, hexadecyl, septadecyl, octadecyl, nonadecyl, and icosyl.

In the context of this invention, the term $(C_2\text{-}C_{20})$-alkenyl shall include all linear or branched compounds of all stereoisomeric conformations of ethylene, propylene, butylene, pentylene, hexylene, heptylene, octylene, nonylene, decylene, undecylene, dodecylene, tridecylene, tetradecylene, pentadecylene, hexadecylene, septadecylene, octadecylene, nonadecylene, and eicosylene.

The invention pertains further to a process for the preparation of myo-inositol-1,2-cyclo-dodecyl-phosphonic acid comprising a] phosphorylation of racemic 1,4,5,6-tetra-O-benzyl-myo-inositol to obtain tetra-O-benzyl-myo-inositol-1,2-cyclo-dodecyl-phosphonic acid; and b] catalytic hydrogenation of tetra-O-benzyl-myo-inositol-1, 2-cyclo-dodecyl phosphonic acid.

Said process for preparation is applicable for manufacturing of any other compound of this invention by using the appropriate starting materials comprising $R_1$, $R_2$, $R_3$, $R_4$, and/or $R_5$ as specified above.

The invention pertains also to a pharmaceutical composition comprising at least one compound selected from the compounds having formula I, their physiologically tolerable salts and the prodrugs thereof and a pharmaceutically acceptable carrier.

The invention pertains further to the use of a compound selected from the compounds having the formula I and their physiologically tolerable salts and prodrugs for changing of the side effects of a medicament which is used for the treatment of diabetes. Such a medicament is e.g. glimepiride. A side effect is e.g. hypoglycaemia caused by a wrong dosage of glimepiride.

The invention pertains also to the use of a compound having the formula I for manufacturing of a pharmaceutical composition for the treatment of side effects of a medicament which is used for the treatment of diabetes (e.g. glimepiride).

The invention refers also to a method for identification of a chemical compound that modulates the activity of glimepiride wherein a] a mammalian cell is incubated with a mix of glimepiride and a chemical compound;

b] hcDIGs of the cells of the product of step a] are prepared;

c] the activity of the GPI-PLC from the hcDIGs of step b] is determined.

A chemical compound in the context of this invention shall mean any organic compound that is either produced by chemical synthesis or isolated from a natural source and has a molecular weight of between 50 and 50,000 Daltons.

The modulation of the activity of glimepiride shall mean that the activity is either stimulated, or inhibited or maintained in sense of stabilizing the activity on a certain level.

The mammalian cell in step a] of the method for identification of a chemical compound that modulates the activity of glimepiride shall encompass the cell of a rodent as e.g. a rat or a mouse, the cell of a dog or the cell of a human. Such cell can be e.g. a pancreatic cell, a muscle cell, a liver cell, a kidney cell, a brain cell or an adipocyte. Also usable is a cell obtained from a cell culture (e.g. primary cell culture). The determination of the activity of GPI-PLC according to step c] of the method for identification of a chemical compound that modulates the activity of glimepiride can be achieved by measuring the dissociation of $pp59^{Lyn}$ from hcDIGs, or by measuring the redistribution of $pp59^{Lyn}$ and/or Gce1 from hcDIGs to lcDIGs, or by measuring the change of phosphorylation of $pp59^{Lyn}$ and/or IRS1, or by measuring the stimulation of glucose transport and/or the inhibition of lipolysis.

If the activity of the GPI-PLC from the hcDIGs according to step c] of the method for identification of a chemical compound that modulates the activity of glimepiride is diminished, the identified chemical compound is inactivating or reducing the activity of glimepiride. If the activity of the GPI-PLC is enhanced, the identified chemical compound is stimulating or supporting the activity of glimepiride.

Salts of chemical compounds of formula I having a pharmaceutically acceptable anion are likewise included in the scope of the invention as useful intermediates for the production or purification of pharmaceutically acceptable salts and/or for use in nontherapeutic, for example in-vitro, applications.

Salts of chemical compounds of formula I can be prepared using customary methods familiar to the person skilled in the art. A salt can be prepared, for example, by combining a chemical compound of formula I with an inorganic or organic acid or base in a solvent or diluent.

The term "physiologically functional derivative" as used herein refers to any physiologically acceptable derivative of a compound of formula I according to the invention, for example an ester, which, upon administration to a mammal, such as, for example, man, is able (directly or indirectly) to form a compound of formula I or an active metabolite thereof.

The physiologically functional derivatives also include prodrugs of the compounds according to the invention. Such prodrugs can be metabolized in vivo to a compound according to the invention. These prodrugs can themselves be active or inactive.

The compounds according to the invention can also be present in various polymorphic forms, for example, as amorphous and crystalline polymorphic forms. All polymorphic forms of the compounds according to the invention are included in the scope of the invention and are a further aspect of the invention.

Hereinbelow, all references to "compound(s) according to formula I refer to a compound/compounds of formula I as described above, and to their salts, solvates and physiologically functional derivatives as described herein.

The amount of a compound according to formula I which is necessary in order to achieve the desired biological effect is dependent on a number of factors, for example the specific compound selected, the intended use, the manner of administration and the clinical condition of the patient. In general, the daily dose is in the range of from 0.3 mg to 100 mg (typically from 3 mg to 50 mg) per day per kilogram of bodyweight, for example 3-10 mg/kg/day. An intravenous dose can be, for example, in the range from 0.3 mg to 1.0 mg/kg, which can be suitably administered as an infusion of 10 ng to 100 ng per kilogram per minute. Suitable infusion solutions for these purposes can contain, for example, from 0.1 ng to 10 mg, typically from 1 ng to 10 mg per milliliter. Individual doses can contain, for example, from 1 mg to 10 g of the active compound. Thus, ampoules for injections can contain, for example, from 1 mg to 100 mg, and orally administrable individual dose formulations, such as, for example, tablets or capsules, can contain, for example, from 1.0 to 1,000 mg, typically from 10 to 600 mg. In the case of pharmaceutically acceptable salts, the abovementioned weight details relate to the weight of the dihydrothiazolium ion derived from the salt. For the prophylaxis or therapy of the abovementioned conditions, the compounds according to formula I can be used themselves as the compound, but they are preferably present in the form of a pharmaceutical composition with a tolerable excipient. The excipient must, of course, be tolerable, in the sense that it is compatible with the other constituents of the composition and is not harmful to the patient's health. The excipient can be a solid or a liquid or both and is preferably formulated with the compound as an individual dose, for example as a tablet, which can contain from 0.05% to 95% by weight of the active compound. Additional pharmaceutically active substances can also be present, including further compounds according to formula (I). The pharmaceutical compositions according to the invention can be prepared by one of the known pharmaceutical methods, which essentially consist of mixing the constituents with pharmacologically acceptable excipients and/or auxiliaries.

Pharmaceutical compositions according to the invention are those which are suitable for oral, rectal, topical, per oral (e.g. sublingual) and parenteral (e.g. subcutaneous, intramuscular, intradermal or intravenous) administration, although the most suitable manner of administration in each individual case is dependent on the nature and severity of the condition to be treated and on the nature of the compound according to formula (I) used in each case. Sugar-coated formulations and sugar-coated delayed release formulations are also included in the scope of the invention. Acid-resistant and enteric-coated formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets, which, in each case, contain a certain amount of the compound according to formula (I); as powders or granules; as solution or suspension in an aqueous or nonaqueous liquid; or as an oil-in-water or water-in-oil emulsion. As already mentioned, these compositions can be prepared by any suitable pharmaceutical method which includes a step in which the active compound and the excipient (which can consist of one or more additional constituents) are brought into contact. In general, the compositions are prepared by uniform and homogeneous mixing of the active compound with a liquid and/or finely divided solid excipient, after which the product is shaped, if necessary. Thus, a tablet, for example, can be prepared by pressing or shaping a powder or granules of the compound, if appropriate with one or more additional constituents. Pressed tablets can be prepared by tableting the compound in free-flowing form, such as, for example, in a powder or granules, if appropriate mixed with a binder, lubricant, inert diluent and/or one (or a number of) surface-active/dispersing agent(s) in a suitable machine. Shaped tablets can be prepared by shaping the pulverized compound or mixture, moistened with an inert liquid diluent, in a suitable machine.

Pharmaceutical compositions which are suitable for peroral (sublingual) administration include lozenges which contain a compound according to formula I with a flavoring agent, customarily sucrose and gum arabic or tragacanth, and pastilles which include the compound in an inert base such as gelatin and glycerol or sucrose and gum arabic.

Suitable pharmaceutical compositions for parenteral administration preferably include sterile aqueous preparations of a compound according to formula I, which are preferably isotonic with the blood of the intended recipient. These preparations are preferably administered intravenously, although the administration can also take place subcutaneously, intramuscularly or intradermally as an injection. These preparations preferably are prepared by mixing the compound with water, and rendering the obtained solution sterile and isotonic with the blood. Injectable compositions according to the invention in general contain from 0.1 to 5% by weight of the active compound.

Suitable pharmaceutical compositions for rectal administration are preferably present as individual dose suppositories. These can be prepared by mixing a compound according to formula (I) with one or more conventional solid excipients, for example cocoa butter, and shaping the resulting mixture.

Suitable pharmaceutical compositions for topical application to the skin are preferably present as ointment, cream, lotion, paste, spray, aerosol or oil. Excipients which can be used include petroleum jelly, lanolin, polyethylene glycols, alcohols and combinations of two or more of these substances. The active compound is, in general, present in a concentration of from 0.1 to 15%, for example of from 0.5 to 2%, by weight of the composition.

Transdermal administration is also possible. Suitable pharmaceutical compositions for transdermal administration can be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from about 1% to 35%, preferably from about 3% to 15%. As a particular possibility, the active compound can be released by electrotransport or iontophoresis, as described, for example, in Pharmaceutical Research, 2(6): 318 (1986).

Examples

Materials and Methods:

Human recombinant insulin, PIG41 (disclosed in "Frick, W. et al., (1998) Biochemistry 37, 13421-13436") and glimepiride (trade name Amaryl) were supplied by the medicinal chemistry and synthesis departments of Aventis Pharma Germany (Frankfurt, Germany). 12-((7-nitrobenz-2-oxa-1,3-diazol-4-yl)amino)dodecanoic acid (NBD-FA) was synthesized as described in Müller et al., (1997) Biochem. Biophys. Acta 1347: 23-39. Collagenase (Worthington, CLS, type I, 250 units/mg) was provided by Biochrom (Berlin, Germany).

Lipoprotein lipase (LPL, affinity-purified) from bovine milk, phospholipase $A_2$ (honey bee venom), crude porcine pancreatic lipase (PL), recombinant PC- and PI-PLC (*Bacillus cereus*), crude PLD (cabbage) and defatted BSA (fraction V) were delivered by SigmalAldrich (Deisenhofen, Germany), crude PI-PLC (rat liver) and proteinase inhibitors were purchased from Roche Molecular Biochemicals (Mannheim, Germany). Recombinant GPI-PLC (*Trypanosoma brucei*) was obtained from Oxford Glycosystems (Oxford, UK). Inhibitors of $PLA_2$ ($AACOCF_3$) and PLC (U 73122) were from Tocris (Avonmouth, UK). Bisbodipy-$C_{11}$-PC was bought from Molecular Probes (Eugene, Oreg.). Lipids were purchased from Avanti Polar Lipids (Birmingham, Ala.). Antibodies for immunoprecipitation of caveolin-1 (clone C060) and immunoblotting of caveolin-1 (rabbit) and $pp59^{Lyn}$ (clone 32) were from Transduction Laboratories (Lexington, Ky.). Antibodies for immunoblotting of phosphotyrosine (clone 4G10) were made available by Upstate Biotechnology (Lake Placid, N.Y.). Antibodies (rabbits, affinity-purified) for immunoblotting of IRS-1 (against total human recombinant protein expressed in insect cells), 5'-Nuc (rat) and aP (bovine) were prepared by Biotrend (Cologne, Germany). ECL Renaissance chemiluminescence detection kit was obtained from NEN/DuPont (Bad Homburg, Germany). Sprague-Dawley rats were provided by Charles-River Laboratories (UK).

Synthesis of GPI-2350 (See Also Draft Scheme in FIG. 1):

As starting material, racemic 1,4,5,6-tetra-O-benzyl-myo-inositol (hereinafter: compound 1) was prepared by a procedure as disclosed in "Zhai, H.-X. et al. (1995) Tetrahedron Lett. 36: 7403-7406". Compound 1 was then phosphorylated with dodecylphosphonic dichloride in the presence of triethylamine and dimethyl-aminopyridine to yield tetra-O-benzyl-myo-inositol-1,2-cyclo-dodecylphosphonic acid (hereinafter: compound 2). By catalytic hydrogenation with 10% Pd on charcoal, compound 2 was debenzylated to myo-inositol-1,2-cyclo-dodecylphosphonic acid (hereinafter: compound 3 or GPI-2350) as a mixture of diastereomers. For synthesis of compound 2 (FIG. 1), 1 g (1.8 mmol) of compound 1 was dissolved in 60 ml of methylene chloride and 1 ml of triethylamine; 200 mg dimethyl-aminopyridine and 1 g (10 mmol) of dodecylphosphonic dichloride were added. This reaction solution was allowed to stand (45 min, room temperature). Then 50 ml of ethyl acetate were added and the mixture was filtered on silica gel. After concentration of the solvent, the residue was purified by flash chromatography (n-heptane/ethyl acetate, 1/1, by vol.). Yield of compound 2: 580 mg (43%) of a white amorphous solid. TLC: n-heptane/ethyl acetate (1/1, by vol.), $R_f$=0.7. MS: $(M+Li)^+$=761.4, calculated $C_{60}H_{59}O_7P$, M=754.9. For synthesis of compound 3 (FIG. 1), 505 mg (0.67 mmol) of compound 2 was dissolved in a mixture of 5 ml of ethyl acetate and 15 ml of methanol. After adding 700 mg of Pd (10%) on charcoal, the reaction mixture was hydrogenated (6 h, 1 atmosphere $H_2$). Pd was filtered over silica gel and washed with 100 ml methanol. After concentration of the solvent, the residue was purified by flash chromatography (methylene chloride/methanol, 5/1, by vol.). Yield of compound 3: 179 mg (68%) of a white amorphous solid. TLC: methylene chloride/methanol (5/1, by vol.), $R_f$=0.15. MS: $(M+Li)^+$=401.2, calculated $C_{18}H_{35}O_7P$, M=394.4. Compound 3 is less stable in acidic than basic solvents. It is stable in methanol for days and as dried amorphous solid for years at 4° C.

Preparation and Incubation of Rat Adipocytes:

Adipocytes isolated by digestion from epididymal fat pads of male rats (120-140 g, fed ad libitum, see Ref. 53 [Muller et al.; Mol. Cell. Biol. 21:4553-4587 (2001)]) were washed twice in KRH (20 mM Hepes/KOH, pH 7.4, 1.2 mM $KH_2PO_4$, 140 mM NaCl, 4.7 mM KCl, 2.5 mM $CaCl_2$, 1.2 mM $MgSO_4$) containing 1% (w/v) BSA and then incubated in the same medium supplemented with 100 μg/ml gentamycin, 100 nM 1-methyl-2-phenylethyladenosine, 0.5 U/ml adenosine deaminase, 1 mM sodium pyruvate and 5 mM D-glucose in the absence or presence of GPI-2350 (prepared as 10 mM stock solution in DMSO, the final DMSO concentration in the in vitro and adipocyte incubations was kept constant at 0.5% at any inhibitor concentration), insulin or glimepiride (prepared as described in "Müller et al. (1994) J. Cell. Biol. 126:1267-1276") at 37° C. in a shaking water bath at constant bubbling with 5% $CO_2$/95% $O_2$ at a final titer of 100 μl of packed cell volume per ml incubation volume (determined by aspiration of small aliquots into capillary hematocrit tubes and centrifugation for 60 s [seconds] in a microhematocrit centrifuge in order to determine the fractional occupation of the suspension by the adipocytes; 10% cytocrit corresponds to about $1.5 \times 10^6$ cells/ml) for the periods indicated.

Preparation of Plasma Membranes and lc/hcDIGs:

Plasma membranes and DIGs were prepared from the post-nuclear infranatant of pre-treated and then washed adipocytes homogenized in lysis buffer (25 mM morpholinoethane-sulfonic acid [MES], pH 6.0, 140 mM NaCl, 2 mM EDTA, 0.5 mM EGTA, 0.25 M sucrose, 50 mM NaF, 5 mM sodium pyrophosphate, 10 mM glycerol-3-phosphate, 1 mM sodium orthovanadate and protease inhibitors) using a motor-driven TEFLON-in-glass homogenizer (10 strokes). Plasma membranes were obtained by differential centrifugation of the defatted postnuclear infranatant and then purified by two sequential centrifugations through sucrose and PERCOLL cushions as described previously (48, 53 [Muller et al. Mol. Med. 8:120-136 (2000)], [Muller et al.; Mol. Cell. Biol. 21:4553-5467 (2001)]) and finally suspended in 25 mM Tris/HCl (pH 7.4), 0.25 M sucrose, 1 mM EDTA at 2 mg protein/ml. hc/lcDIGs were obtained by the detergent method and discontinuous sucrose gradient centrifugation as reported in "Müller, G. et al (2002) Mol. Med. 8: 120-136". The light-scattering opalescent bands at the 15-22% (fractions 4-5) and 28-35% (fractions 8-9) sucrose interfaces were collected as hcDIGs and lcDIGs, respectively, with density measurement using the refractive index. hc/lcDIGs were collected by centrifugation (50,000×g, 30 min, 4° C.) after three-fold dilution of the pooled gradient fractions with 25 mM MES (pH 6.5), 1% Triton X-100, 150 mM NaCl, and then characterized (immunoblotting, enzyme assays) by enrichment/deprivation of relevant markers as described in "Müller, G. et al (2002) Mol. Med. 8: 120-136" and/or "Müller, G. et al. (2001) Mol. Cell. Biol. 21: 4553-4587" or subjected to Triton X-114 partitioning (see below). For immunoprecipitation of caveolin, DIGs were solubilized (1 h, 4° C.) in 10 mM Tris/HCl (pH 7.4), 150 mM NaCl, 1% Triton X-100, 60 mM b-octylglucoside, 0.3% deoxycholate, 5 mM EDTA, 0.5 mM EGTA, 1 mM sodium orthovanadate, 50 mM NaF, 1 μM microcystine and protease inhibitors) and centrifuged (50,000×g, 30 min). For direct immunoblotting, DIGs were solubilized in 2-fold Laemmli sample buffer and centrifuged (10,000×g, 5 min). The supernatants were used.

GPI-PLC/D Assays:

GPI-PLD (rat serum) was assayed according to "Hari et al. (1997) Biochim. Biophys. Acta 1355: 293-302" by incubation with 10 μl of human placental aP solution (100 U/ml in 10 mM Hepes/NaOH, pH 7.0, 150 mM NaCl) in 100 μl of 200 mM Tris/maleate (pH 7.0) and 1% Nonidet P-40 for 10 min at 37° C. and subsequent termination of the reaction by addition of 0.4 ml of ice-cold stop buffer (10 mM Hepes/NaOH, pH 7.0, 150 mM NaCl, 0.1 mM $MgCl_2$ and 0.01 mM zinc acetate). GPI-PLC (*T. brucei*) was assayed as described in "Mensa-Wilmot et al. (1995) Methods Enzymol. 250: 641-655" by incubation with 5 μl of human placental aP solution (see above) in 50 μl of 50 mM Tris/HCl (pH 8.0), 0.25% Nonidet P-40 and 5 mM EDTA for 30 min at 37° C. and subsequent termination of the reaction by addition of 0.45 ml of stop buffer. PI-PLC (*B. cereus*) and adipocyte GPI-PLC (5-25 μg plasma membranes or hc/lcDIGs) were assayed by incubation with 10 μl of bovine erythrocyte acetylcholinesterase (AChE) solution (12 U/ml in 10 mM Tris/HCl, pH 7.4, 144 mM NaCl, 0.1% TX-100) in 100 μl of 20 mM Hepes/KOH (pH 7.8), 144 mM NaCl, 0.1% TX-100, 0.2 mM $MgCl_2$ for 1 h at 25° C. and subsequent termination by adding 5 μl of glacial acetic acid and then 0.4 ml of 10 mM Tris/HCl (pH 7.4), 144 mM NaCl. Each reaction mixture was subjected to TX-114 partitioning (see below). The GPI-PLC/D activity was calculated from the ratio of the activities of hydrophilic aP or AChE measured in the TX-114-depleted phase and the total activity measured before partitioning and corrected for the non-enzymatic background in the TX-114-depleted phase (accounting for 10-20% of the total activity) as revealed by blank incubations lacking (G)PI-PLC/D.

Other Lipase Assays:

Hormone-sensitive lipase (HSL) and lipoprotein lipase (LPL) were measured using a radiolabeled triolein droplet emulsion as described in "Vertesy et al., (2002) Journal Antibiotics 55:480-494". Pancreatic lipase (PL) was determined by incubation of 0.25 mmol tributyrin in 2 ml of 5 mM Tris/HCl (pH 6.5), 6 mM sodium taurodeoxycholate, 150 mM NaCl, 1 mM $CaCl_2$ with porcine PL and colipase in the same buffer using a recording pH stat (stirring at 1000 rpm at 25° C.) with the pH adjusted to 6.5. PC-PLC was assayed by incubation of 0.2 ml of 10 mM dipalmitoyllecithin, 0.1 ml of 10 mM SDC and 0.1 ml of 0.03 M $CaCl_2$ with bacterial PC-PLC (in 50 mM Tris/HCl, pH 7.5, 0.1% BSA) for 10 min at 37° C. The reaction was terminated by addition of 0.1 ml of 50% TCA and subsequently of 2.5 ml of chloroform/methanol (66/33/1, by vol.). After centrifugation (1500×g, 15 min), 0.2-ml portions of the upper methanol/water phase (~1.33 ml) were removed, supplemented with 0.5 ml of 60% $HClO_4$, then heated at 170° C. for 1 h and finally analyzed for inorganic phosphate. Mammalian PI-PLC was measured by incubation of 0.1 ml of 10 mM PI, 0.1 ml of 0.8% sodium deoxycholate, 0.1% BSA, 0.2 ml of 100 mM sodium borate (pH 7.5) and rat liver PI-PLC for 20 min at 37° C. The reaction was terminated and further processed as described for the PC-PLC. PLD was assayed with 1.6 mM [U-$^{14}$C]phosphatidylcholine (~2000-4000 dpm/nmol) in 250 μl of 40 mM Hepes/KOH (pH 6.0), 4 mM $CaCl_2$ and cabbage PLD. After incubation for 30 min at 37° C., the reaction was terminated by addition of 5 ml of chloroform/methanol (2/1, by vol.) containing carrier phosphatidic acid. After removal of water-soluble material, lipids contained in the final washed lower chloroform phase were transferred to a heat-activated silica gel plate and separated two-dimensionally using chloroform/methanol/ammonia (65/35/4, by vol.) in the first and chloroform/acetone/methanol/acetic acid/water (50/20/10/10/5, by vol.) in the second dimension. Radioactive phosphatidic acid was detected by phosphorimaging. $PLA_2$ was determined according to "Kim, T.-S. et al., (1997) J. Biol. Chem. 272: 2542-2550" with a unilamellar liposomal substrate consisting of 1-palmitoyl-2-palmitoyl-sn-glycerol-3-phosphocholine/bisbodipy-$C_{11}$-PC/phosphatidyl-glycerol/cholesterol (10/0.05/2/3, by vol.). Concentration-response curves were fitted using a Marquardt-Levenberg non-linear least squares algorithm. When plotted on log-linear axes, this equation results in sigmoidal curves (SigmaPlot software, Jandel Scientific).

Immunoprecipitation of Caveolin:

Solubilized DIGs (see above, 5-20 μg protein) were precleared by incubation with protein A/G-Sepharose and subsequent centrifugation (10,000×g, 5 min). The supernatant was incubated with anti-caveolin-1 antibodies (1:1000) preadsorbed on protein A/G-Sepharose in 1 ml of 10 mM Tris/HCl (pH 7.4), 150 mM NaCl, 1% TX-100 for 1 h at 4° C. The immune complexes were washed twice with the same buffer and then twice with buffer lacking TX-100 and finally subjected to SDS-PAGE performed in the absence of β-mercaptoethanol. The recovery of immunoprecipitated caveolin was normalized by homologous immunoblotting with anti-caveolin antibodies of the same blot following stripping of the membrane.

Immunoblotting:

Polypeptides separated by SDS-PAGE were transferred to polyvinylidene difluoride membranes using the semidry procedure as described in "Müller, G. et al., (2001) Mol. Cell. Biol. 21: 4553-4567". Washed membranes were incubated with anti-caveolin-1 (1:2000), anti-pp59$^{Lyn}$ (1:1250), anti-aP (1:500), anti-5'-Nuc (1:750) and anti-IRS-1 (1:2000) antibodies for 4 h at 15° C. Washed membranes were incubated with horseradish peroxidase-coupled secondary goat anti-mouse (1:2000) or goat anti-rabbit IgG (1:4000) antibodies. Labeled proteins were visualized by enhanced chemiluminescence.

TX-114 Partitioning:

Pelleted hc/lcDIGs (10-50 μg protein) or (G)PI-PLC reaction mixtures (0.5 ml) were separated into amphiphilic and hydrophilic proteins using partitioning between TX-114-enriched and depleted phases according to "Bordier, C., (1981) J. Biol, Chem. 272: 2542-2550" by suspending in 1 ml of ice-cold TX-114 (1%), 25 mM Tris/HCl (pH 7.4), 144 mM NaCl or mixing with 0.5 ml of ice-cold TX-114 (2%), respectively. After incubation for 1 h on ice, the mixture was layered onto a cushion of 0.4 ml of 0.25 M sucrose and 25 mM Tris/HCl (pH 7.4) on ice. Phase separation was induced by warming up to 37° C. and subsequent centrifugation (10,000×g, 1 min). After re-extraction of the lower TX-114-enriched phase, aliquots of the pooled upper TX-114-depleted phase were measured for 5'-Nuc, aP and AChE activity or precipitated (15 polyethylene glycol 4000) for SDS-PAGE analysis.

Glucose Transport Assay:

Glucose transport was determined as described in "Müller, G. et al., (1994) J. Cell Biol. 126: 1267-1276" by incubation of 10,000-20,000 washed adipocytes with 2-deoxy-D[2,6-$^3$H]glucose at 50 μM final conc. (0.33 μCi/ml) in 50-μl portions for 20 min at 37° C. in the absence or presence of 20 μM cytochalasin B.

Miscellaneous Procedures:

Electroporation was performed as described in "Müller, G. et al., (2000) Mol. Cell. Biol. 20: 4708-4723". Lipolysis was determined as release of glycerol or fluorescent NBD-FA from prelabeled and isoproterenol-stimulated adipocytes as described in "Müller, G. et al., (2003) Biochimie 85: 1245-1256". Gce1 was detected by photolabeling of solubilized plasma membranes or hc/lcDIGs (10-50 μg protein) with 8-$N_3$—[$^{32}$P]cAMP and subsequent phosphorimaging as described in "Müller, G. et al., (1994) Biochemistry 33: 12149-12159". 5'-Nuc, aP and AChE activities were measured according to "Eliakim, R. et al., (1990) Biochim. Biophys. Acta 1355: 293-302". Protein was determined using the BCA protein determination kit from Pierce (Rockford, Ill.) and BSA as calibration standard. SDS-PAGE was performed using precast gels (Novex, San Diego, Calif.; 10% Bis-Tris resolving gel, morpholinopropanesulfonic acid-SDS running buffer). Lumiimages were evaluated on a LumiImager using LumiImager software (Roche Diagnostics). Phosphor- and fluorescence images were processed and quantified using the Storm 860 PhosphorImager system (Molecular Dynamics, Gelsenkirchen, Germany). Figures were constructed using the ADOBE PHOTOSHOP software (Adobe Systems, Mountain View, Calif.).

GPI-2350 Inhibits (G)PI-PLC/D of Various Origin with High Potency and Selectivity:

The effect of GPI-2350 on (purified or crude) B. cereus PI-PLC, T. brucei GPI-PLC and rat serum GPI-PLD was monitored by their incubation with partially purified solubilized GPI proteins under appropriate conditions (low or high detergent conc.) in the presence of increasing concentrations of GPI-2350. Subsequently, the ratio of hydrophilic GPI-protein harboring the lipolytically cleaved GPI anchor in the digestion mixtures relative to the total GPI-proteins was determined by measurement of the enzymatic activity in the detergent-depleted phases upon TX-114 partitioning and in the total digestion mixture before partitioning, respectively (FIG. 2). GPI-2350 inhibited bacterial, trypanosomal and serum (G)PI-PLC/D with apparent $IC_{50}$ of 10, 2 and 1 µM, respectively. GPI-2350 also blocked the rat adipocyte GPI-PLC with $IC_{50}$ of 0.2-0.5 µM using as enzyme source solubilized plasma membranes, IcDIGs or hcDIGs and as substrate, AChE. To demonstrate the cleavage specificity of the adipocyte GPI-PLC, we used the GPI-protein, Gce1, prepared from Saccharomyces cerevisiae spheroblasts which had been metabolically labeled with myo-[$^{14}$C]-inositol. Incubation with hcDIGs led to generation of a hydrophilic and $^{14}$C-labeled version of Gce1, which was immunoprecipitated with anti-CRD antibodies raised against cIP, in concentration- and time-dependent fashion (data not shown). The hcDIG-dependent generation of a GPI-protein lacking fatty acyl chains and harbouring cIP confirms the expression of a GPI-PLC in the plasma membrane of rat adipocytes.

Next, the selectivity of GPI-2350 was studied. Several neutral lipases (HSL, PL, LPL) and PC/PI-specific phospholipases of different specificity ($A_2$, C, D) from various sources as well as bovine AChE, which were all known to operate via the so-called catalytic triad, were not significantly affected under conditions (50 µM) which blocked the bacterial, trypanosomal, serum and rat adipocyte GPI-PLC/D by 60 to 95% (FIG. 3). Two derivatives of GPI-2350 harbouring open instead of cIP, 2-deoxy-2-fluoro-scyllo-inositol-1-O-dodecyl-phosphonic acid (GPI-1793) and myo-inositol-1-O-dodecylphosphonic acid methylester (GPI-2349), had a moderate to very moderate effect, respectively, on the adipocyte GPI-PLC at the highest concentration tested, only, but inhibited the bacterial and trypanosomal (G)PI-PLC with similar potencies (Tab. 1). These findings demonstrate the similarity in the catalytic mechanism involving generation of stable or transient 1,2-cyclic phosphate bonds, but also for some differences in substrate recognition between bacterial, trypanosomal and adipocyte (G)PI-PLC. Assuming that the latter operates via a cIP intermediate and on basis of preliminary kinetic studies, it must be assumed that GPI-2350 acts as a competitive inhibitor ($K_i$=3-20 µM). This may explain its pronounced selectivity, since neutral lipases and mammalian PC/PI-specific phospholipases do not recognize GPI structures. In agreement with a competitive mode of action, half-maximal inhibition of bacterial and trypanosomal (G)PI-PLC by GPI-2350 was completely reversed upon 10-fold dilution of the reaction mixture with excess of fresh GPI-protein substrate. In contrast, adipocyte hcDIGs treated with 50 µM GPI-2350 prior to reisolation and extensive washing exhibited only low lipolytic cleavage toward purified solubilized AChE upon incubation in the absence of GPI-2350 (data not shown). This may be explained by interaction of amphiphilic GPI-2350 with hcDIGs. Alternatively, GPI-2350 may act as a transition state analog and undergo (transient) covalent coupling to the active site of the adipocyte GPI-PLC. It would be interesting to know whether the cyclic phosphate bond of GPI-2350 is opened by the (G)PI-PLC/D.

GPI-2350 Blocks Insulin- and Glimepiride-Induced Cleavage of GPI-Proteins in Isolated DIGs and Intact Adipocytes:

On the basis of the observed interference of GPI-2350 with cleavage of GPI-proteins by adipocyte plasma membrane GPI-PLC in vitro when both are presented in separate complexes (detergent micelles and DIGs, respectively), we next studied the efficacy of GPI-2350 on basal and stimulated GPI-PLC activity in intact adipocytes and isolated DIGs with endogenous or exogenous GPI-proteins as substrate (FIG. 4). In isolated rat adipocytes, the GPI-PLC activity (followed as cleavage of endogenous 5'-Nuc, Gce1 and aP by monitoring their amphiphilic-to-hydrophilic conversion) was stimulated by both glimepiride and insulin (up to 5- and 3-fold, respectively)(Panels E, G). The stimulation was partially preserved in hcDIGs prepared from these pretreated adipocytes (3- and 1.7-fold, respectively)(Panel C). Remarkably, the GPI-PLC was activated by direct incubation of hcDIGs prepared from untreated adipocytes with glimepiride (up to 4-fold), but not insulin (Panel A). GPI-2350 reduced the basal as well as glimepiride- and insulin-stimulated GPI-PLC activity in concentration-dependent fashion to lower than basal and similar levels in both isolated hcDIGs and intact adipocytes (FIG. 4, all panels). Apparently, GPI-2350 does not interfere with activation of the GPI-PLC, since the inhibitor was present prior to and during incubation with insulin or glimepiride (Panels C, E). The $IC_{50}$ for inhibition of the GPI-PLC when assayed with intact adipocytes (5-10 µM, Panel F) was higher compared to isolated intact hcDIGs (1 µM, Panels B, D) as well as solubilized hcDIGs and plasma membranes (0.2-0.5 µM, FIG. 2). This may reflect impaired accessibility of the catalytic site of the GPI-PLC for GPI-2350 when embedded within DIGs in the plasma membrane of intact adipocytes compared to isolated DIGs. However, the need for cellular permeation of GPI-2350, which, on the basis of its amphiphilic nature, is predicted to be rather high, can presumably be excluded since the major substrates of the GPI-PLC, GPI lipids and protein anchors are localized at the outer leaflet of the plasma membrane and GPI-2350 is likely to act as (competitive) inhibitor of the catalytic site of the GPI-PLC (see above). Rather, it is conceivable that GPI-2350 via its dodecyl chain spontaneously partitions into non-DIG areas of the adipocyte plasma membrane (comprising 80-90% of the total cell surface) similar to detergents which partition preferentially into the disordered domains of non-DIG areas rather than liquid-ordered domains of DIGs.

Under the experimental conditions used for the isolation of DIGs and plasma membranes, 65-85% of the GPI-PLC activity (measured as cleavage of exogenous AChE) in isolated total plasma membranes was recovered with DIGs (i.e. hcDIGs plus IcDIGs) irrespective of the treatment of the adipocytes. Similar recoveries were observed for the typical DIGs marker protein, caveolin-1 (70-90%), as determined by immuno-blotting and the DIGs resident protein, p115 (55-75%) as determined by binding of synthetic PIG. Moreover, the total amounts of aP, 5'-Nuc and Gce1 (amphiphilic plus hydrophilic versions) recovered with DIGs (hcDIGs plus IcDIGs) from the differentially treated adipocytes were roughly constant (90-140% with basal set at 100%), demonstrating the reproducibility of the DIGs isolation procedure under the various conditions. Since isolated hcDIGs are characterized by a considerably lower protein content than lcDIGs and non-DIG areas, the GPI-PLC is highly enriched in hcDIGs vs. the residual plasma membrane, consistent with the localization of the GPI-protein substrates.

GPI-PLC Action in Rat Adipocytes is Required for Redistribution of GPI-Anchored and Acylated Signaling Proteins within DIGs:

We next investigated whether inhibition of lipolytic cleavage of GPI-proteins affects the localization and stimulus-dependent redistribution of GPI-anchored as well as acylated signaling proteins within DIGs of the adipocyte plasma membrane. For this, hc/lcDIGs were prepared from adipocytes which had been incubated in the absence or presence of GPI-2350 prior to challenge with glimepiride and then analyzed for the presence of several GPI-anchored or acylated signaling proteins (FIG. 5). The robust redistribution of pp59$^{Lyn}$, Gce1 and 5'-Nuc from hcDIGs to lcDIGs in response to glimepiride as manifested in the 3- to 5-fold increases in their amounts at lcDIGs, which corresponded to 70 to 90% losses at hcDIGs compared to basal adipocytes, was almost completely abolished in the presence of max. effective conc. of GPI-2350. In contrast, the relative enrichment of the hcDIGs resident proteins, caveolin-1 and IRβ, at hcDIGs vs. lcDIGs as well as the similar abundance of the glucose transporter isoform 4 (Glut4) at hcDIGs and lcDIGs, both of which were not affected by glimepiride, did not alter significantly in the presence of GPI-2350 (FIG. 5). This demonstrates that potent inhibition of the GPI-PLC specifically interferes with the stimulus-dependent translocation of certain lipid-modified signaling proteins, such as Gce1 and pp59$^{Lyn}$, from hcDIGs to lcDIGs rather than causing general and unspecific changes in the structure of DIGs.

Next, we studied the mechanism underlying the putative causal relationship between GPI-PLC action and GPI-protein redistribution, i.e. whether the lipolytically cleaved and/or uncleaved GPI-proteins are actually translocated to lcDIGs in stimulated isolated rat adipocytes. For this, rat adipocytes were incubated with or without GPI-2350 and then challenged with insulin or glimepiride. The amounts of hydrophilic and amphiphilic versions of the GPI-proteins, 5'-Nuc, aP and Gce1, recovered from total plasma membranes, hcDIGs and lcDIGs, were determined by TX-114 partitioning (Tab. 2). Treatment with insulin and, more potently, glimepiride led to an increase in hydrophilic GPI-proteins in plasma membranes, which was completely blocked by GPI-2350, demonstrating efficient GPI-PLC inhibition. In response to both insulin and glimepiride, the increase in the amount of hydrophilic GPI-proteins was detected at hcDIGs, exclusively, and was accompanied by a decrease in the amphiphilic versions at the same location. These changes were reversed even below basal values in the presence of GPI-2350, demonstrating the lipolytic nature of this amphiphilic-to-hydrophilic conversion. Thus, hydrophilic GPI-proteins generated by the insulin/glimepiride-stimulated GPI-PLC at hcDIGs remain associated with hcDIGs via a molecular mechanism not relying on the GPI anchor (Tab. 2). Interestingly, the glimepiride-induced redistribution of 5'-Nuc, Gce1 and aP from hcDIGs to lcDIGs (see FIG. 5) was restricted to their uncleaved versions, as reflected in the 3- to 4-fold elevated levels in the amphiphilic but unaltered low levels in the hydrophilic GPI-proteins recovered with lcDIGs, but nevertheless completely eliminated by GPI-2350 (Tab. 2). In contrast, the insulin-induced generation of hydrophilic 5'-Nuc, Gce1 and aP was accompanied by a very moderate increase (border of significance) of their amphiphilic counterparts at lcDIGs, only, which again was abrogated in the presence of GPI-2350. All three GPI-proteins studied displayed the correlation between stimulus-dependent lipolytic cleavage and redistribution of their amphiphilic versions, exclusively, with only minor quantitative differences (Tab. 2). Taken together, GPI-PLC activation for generation and accumulation of lipolytically cleaved GPI-proteins at hcDIGs is required (glimepiride).

Inhibition of the GPI-PLC Interferes with the Dissociation of GPI-Anchored and Acylated Signaling Proteins from Caveolin:

The redistribution of signaling proteins from hcDIGs to lcDIGs in rat adipocytes has recently been shown to be accompanied by their dissociation from caveolin-1 and activation. Next we investigated the putative causal relationship between dissociation from caveolin/activation and stimulus-dependent lipolytic cleavage of GPI-proteins in rat adipocytes by inhibiting GPI-PLC and subsequent analysis of the interaction with caveolin-1 of Gce1 and pp59$^{Lyn}$ as well as kinase activity of the latter (FIG. 6). The insulin- (35-45%) and glimepiride- (75-85%) induced maximal losses of both pp59$^{Lyn}$ and Gce1 from caveolin-1 immunoprecipitates prepared from isolated and solubilized hcDIGs were completely abrogated by GPI-2350 (50 μM; FIG. 6, Panel A) with IC$_{50}$ of 5-10 μM (Panel B). This potency is similar to GPI-PLC inhibition by GPI-2350 in intact adipocytes (FIG. 3). The binding of the scaffolding domain of caveolin-1 (CSD) to the caveolin-binding domain (CBD) of signaling proteins, such as non-receptor tyrosine kinases, and conversely relief of the CSD from binding to the CBD have been shown in many but not all cases to trigger inactivation and activation, respectively, of the signalling proteins in in vitro assays. This implies a regulatory function of the CSD-CBD interaction in signal transduction operating at plasma membrane DIGs.

Inhibition of the GPI-PLC in Rat Adipocytes Downregulates the Metabolic Activity of Glimepiride but not Insulin:

Subsequently, we studied whether the differential effects of GPI-PLC inhibition on IRS-1 tyrosine phosphorylation in response to insulin and glimepiride is reflected in their metabolic activity in insulin target cells. For this, isolated rat adipocytes were pretreated with GPI-2350 prior to challenge with either stimulus, and then assayed for glucose transport and isoproterenol-induced lipolysis (FIG. 8). The stimulation of glucose transport and inhibition of isoproterenol-induced lipolysis by glimepiride was impaired in the presence of GPI-2350 in concentration-dependent fashion (IC$_{50}$=2-5 μM) to lower than control values (at 50 μM). Consequently, the glimepiride concentration-response curves were shifted to the right and became flattened in the course of half-maximal inhibition of the GPI-PLC by GPI-2350 (5 μM) compared to the absence of inhibitor. In contrast, insulin stimulation of glucose transport and inhibition of isoproterenol-induced lipolysis, being 2- to 3-fold more pronounced compared to glimepiride, were reduced by GPI-2350 by up to 25 and 33%, respectively, at 50 μM, only (FIG. 8). These differential effects of GPI-PLC inhibition were confirmed by analysis of the effect of GPI-2350 on the inhibition of isoproterenol-induced lipolysis by glimepiride and insulin when measured as release of NBD-FA instead of glycerol from rat adipocytes prelabeled with this fluorescent fatty acid derivative (FIG. 9). The reduction in the amount of NBD-FA including its oxidative degradation products being released from isoproterenol-induced adipocytes in response to increasing concentrations of glimepiride (10$_{50}$=3 μM) was completely abrogated in the presence of 50 μM glimepiride (Panels A, B). In contrast, insulin inhibition of NBD-FA (and degradation products) release was impaired by up to 25-30%, only, by GPI-2350 (50 μM) accompanied by a minor increase in the apparent $IC_{50}$ for insulin (0.1 vs. 0.3 µM). The specificity of these GPI-2350-mediated effects for GPI-PLC inhibition was confirmed by the failure of inhibitors of rat liver PI-PLC and bee venom $PLA_2$ to significantly affect basal and glimepiride-regulated glucose transport and lipolysis (FIG. 8).

Finally, the involvement was investigated of the GPI-PLC in signaling pathways of insulin-mimetic stimuli other than glimepiride, which are either dependent on or independent of the redistribution of GPI-proteins within DIGs. In rat adipocytes, disruption of hcDIGs by cholesterol depletion using m-B-CD, inactivation of the PIG receptor, p115, by trypsin-/salt-/NEM-treatment or occupancy of p115 with the synthetic ligand, PIG41, led to pronounced increases of 5'-Nuc at IcDIGs and glucose transport activation (Tab. 3). In contrast, sodium orthovanadate as well as synthetic CBDP stimulated glucose transport without concomitant induction of 5'-Nuc translocation to IcDIGs. This is in agreement with their modes of action, the well-known inhibition of insulin receptor and IRS-1 dephosphorylation by the tyrosine phosphatase inhibitor, vanadate and the direct stimulation of $pp59^{Lyn}$ and IRS-1 tyrosine phosphorylation by the CBDP. Stimulation of neither IRS-1 tyrosine phosphorylation nor glucose transport (Tab. 3) by these stimuli was affected significantly in the presence of GPI-2350, implying that they all cross-talk to the glucose transport system at a point downstream of the GPI-PLC.

Description of Tables:

Tab. 1: Characteristics of (G)PI-PLC inhibitors.

Tab. 2: Effect of insulin, glimepiride and GPI-2350 on the localization of lipolytically cleaved and uncleaved GPI-proteins at hcDIGs, IcDIGs and total plasma membranes.

Tab. 3: Effect of GPI-2350 on 5'-Nuc translocation and glucose transport induced by various insulin-mimetic stimuli in rat adipocytes.

Legends to Tables

Table 1: GPI-PLC of hcDIGs from rat adipocytes, GPI-PLC from *T. brucei* and PI-PLC from *B. cereus* were incubated with solubilized and partially purified bovine erythrocyte AChE or human placental aP in the absence or presence of increasing concentrations (0.05 µM-1 mM) of the inhibitors indicated under appropriate conditions (see Materials and Methods). Cleavage rate was calculated from the amount of hydrophilic AChE and aP activity recovered with the TX-114-depleted phase upon TX-114 partitioning. Means+SD from at least 3 independent incubations with partitioning/enzyme assays in quadruplicate are given. n.a., not applicable.

Table 2: Isolated rat adipocytes were treated (5 min, 37° C.) without or with GPI-2350 (50 µM) and then incubated (120 min, 37° C.) in the absence or presence of glimepiride (20 µM) or insulin (10 nM) as indicated. Total plasma membranes (PM), hcDIGs and IcDIGs were prepared and then subjected to TX-114 partitioning. The TX-114-enriched and depleted phases were assayed for 5'-Nuc and aP (activity measurement) and Gce1 (photoaffinity-labeling). The amounts of amphiphilic and hydrophilic GPI-protein were calculated relative to the amphiphilic version in total plasma membranes and hcDIGs, respectively, prepared from basal adipocytes in the absence of GPI-2350 (set at 100 arb. units each). The recoveries of the hydrophilic and amphiphilic GPI-proteins from hcDIGs plus IcDIGs were comparable under the various incubation conditions. Means±SD of at least 3 independent cell incubations with activity measurements/gel runs in duplicate each are given.

Table 3: Isolated rat adipocytes were incubated in the presence of methyl-β-cyclodextrin (m-β-CD, 10 mM, 50 min), CBDP (300 µM, electroporation, followed by washing and subsequent incubation for 30 min), PIG41 (10 µM, 15 min), sodium orthovanadate (1 mM, 15 min), trypsin (10 µg/ml, 15 min followed by treatment with 0.5 M NaCl and subsequent washing) and N-ethylmaleimide (1 mM, 5 min followed by addition of DTT). After addition of GPI-2350 (50 µM final conc.) to one half of the adipocyte suspension and further incubation (60 min, 37° C.), portions of the cells were assayed for 5'-Nuc activity in the isolated IcDIGs. The increase in 5'-Nuc during the basal incubation was set at 100 arb. units. Other portions of the cells (after 15 min incubation) were assayed for glucose transport which was set at 100 arb. units for the basal incubation. Means+SD of at least 3 independent cell incubations with activity measurements in triplicate each are given.

TABLE 1

| | GPI-2350 | | GPI-1793 | | GPI-2349 | |
|---|---|---|---|---|---|---|
| | $IC_{50}$ [µM] | inhibition % at 1 mM | $IC_{50}$ [µM] | inhibition % at 1 mM | $IC_{50}$ [µM] | inhibition % at 1 mM |
| GPI-PLC adipocytes | 0.2-0.5 | 95 + 11 | n.a. | 42 + 5 | n.a. | 27 + 6 |
| GPI-PLC *T. brucei* | 2-5 | 85 + 9 | 25-35 | 89 + 7 | 310-390 | 66 + 8 |
| PI-PLC *B. cereus* | 10-20 | 75 + 8 | 110-140 | 70 + 10 | n.a. | 24 + 5 |

TABLE 2

| | | Treatment of Rat Adipocytes | | | | | |
|---|---|---|---|---|---|---|---|
| | | Basal | Basal GPI-2350 | Insulin | Insulin GPI-2350 | Glimepiride | Glimepiride GPI-2350 |
| 5'-Nuc | hydroph. PM | 7 ± 2 | 3 ± 2 | 14 ± 5 | 2 ± 1 | 19 ± 5 | 6 ± 3 |
| | hydroph. hcDIGs | 13 ± 4 | 7 ± 3 | 34 ± 8 | 8 ± 2 | 48 ± 10 | 10 ± 2 |
| | amphiph | 100 ± 21 | 112 ± 19 | 81 ± 17 | 119 ± 22 | 35 ± 10 | 121 ± 13 |
| | hydroph. IcDIGs | 4 ± 2 | 3 ± 1 | 7 ± 2 | 5 ± 3 | 9 ± 3 | 12 ± 3 |
| | amphiph | 19 ± 5 | 15 ± 6 | 28 ± 4 | 10 ± 13 | 59 ± 9 | 17 ± 4 |
| Gce1 | hydroph. PM | 19 ± 3 | 6 ± 3 | 29 ± 7 | 12 ± 5 | 40 ± 11 | 8 ± 6 |
| | hydroph. hcDIGs | 30 ± 8 | 21 ± 7 | 58 ± 12 | 17 ± 5 | 69 ± 9 | 15 ± 5 |
| | amphiph | 100 ± 12 | 109 ± 10 | 64 ± 8 | 108 ± 13 | 25 ± 10 | 112 ± 10 |

TABLE 2-continued

| | | Basal | Basal GPI-2350 | Insulin | Insulin GPI-2350 | Glimepiride | Glimepiride GPI-2350 |
|---|---|---|---|---|---|---|---|
| | | | | Treatment of Rat Adipocytes | | | |
| | hydroph. lcDIGs | 10 ± 4 | 14 ± 7 | 19 ± 5 | 15 ± 3 | 12 ± 5 | 24 ± 7 |
| | amphiph | 23 ± 8 | 28 ± 6 | 35 ± 9 | 25 ± 6 | 79 ± 15 | 21 ± 7 |
| aP | hydroph. PM | 5 ± 3 | 4 ± 3 | 31 ± 6 | 11 ± 4 | 54 ± 12 | 14 ± 4 |
| | hydroph. hcDIGs | 21 ± 4 | 10 ± 1 | 69 ± 8 | 8 ± 4 | 88 ± 19 | 4 ± 3 |
| | amphiph | 100 ± 14 | 117 ± 11 | 44 ± 7 | 121 ± 12 | 10 ± 3 | 132 ± 19 |
| | hydroph. lcDIGs | 5 ± 1 | 2 ± 2 | 4 ± 2 | 9 ± 2 | 10 ± 2 | 4 ± 2 |
| | amphiph | 14 ± 2 | 19 ± 13 | 27 ± 5 | 10 ± 4 | 49 ± 8 | 10 ± 5 |

TABLE 3

| | Increase in 5'-Nuc at lcDIGs (basal set at 100 arb. units) | | Glucose Transport (basal set at 100 arb. units) | |
|---|---|---|---|---|
| | −GPI-2350 | +GPI-2350 | −GPI-2350 | +GPI-2350 |
| m-β-CD | 595 + 128 | 539 + 104 | 289 + 13 | 249 + 18 |
| CBDP | 128 + 41 | 107 + 59 | 468 + 37 | 515 + 49 |
| PIG41 | 773 + 195 | 894 + 201 | 1264 + 91 | 1195 + 79 |
| sodium orthovanadate | 93 + 38 | 105 + 34 | 707 + 51 | 673 + 45 |
| trypsin/NaCl | 461 + 92 | 530 + 102 | 361 + 40 | 313 + 29 |
| N-ethylmaleimide | 292 + 60 | 319 + 52 | 308 + 33 | 288 + 40 |

Figure 1:
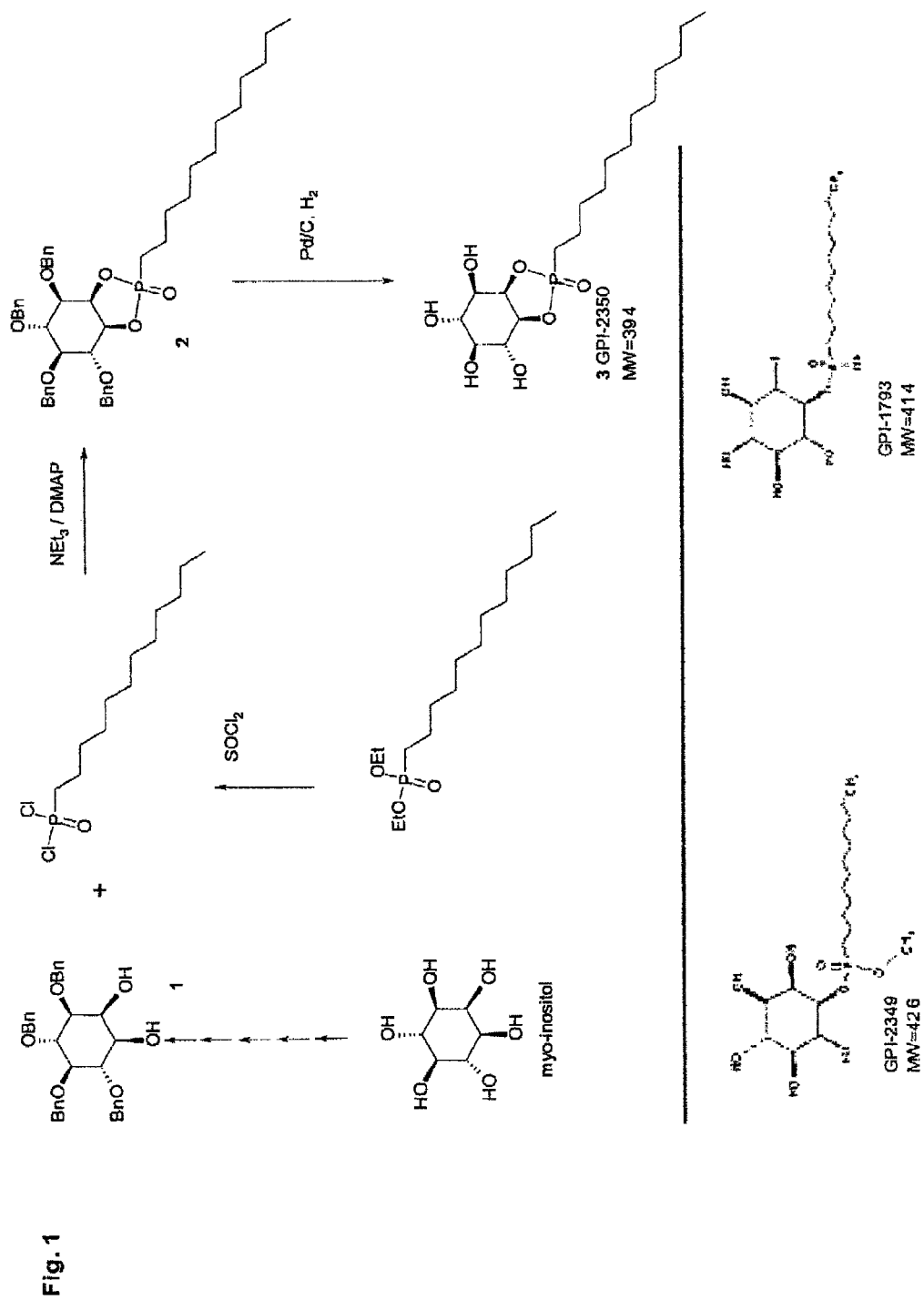
FIG. 1: Structure and synthesis of (G)PI-PLC inhibitors. See Materials and Methods.
Figure 2:
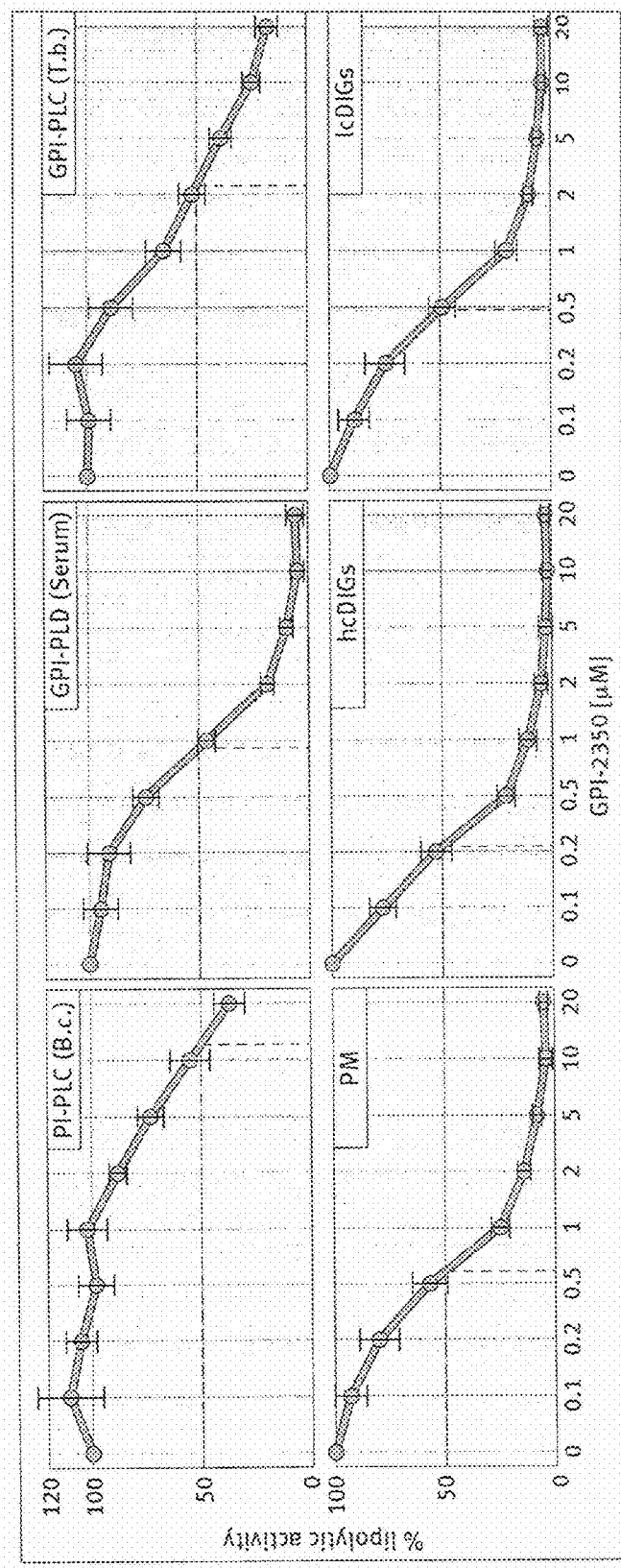
FIG. 2: Potency of GPI-2350. Purified (G)PI-PLC/D from *B. cereus*, rat serum and *T. brucei* as well as total plasma membranes (PM) and hc/lcDIGs prepared from isolated rat adipocytes were incubated (10 min, 30° C.) with increasing concentrations of GPI-2350 and then assayed for amphiphilic-to-hydrophilic conversion of AChE and aP by TX-114 partitioning (see Materials and Methods). The lipolytic activity was calculated as % of the control reaction in the absence of GPI-2350 (set at 100%). Means+SD of at least 4 independent incubations with AChE and aP activity measurements in triplicate each are given.
Figure 3:
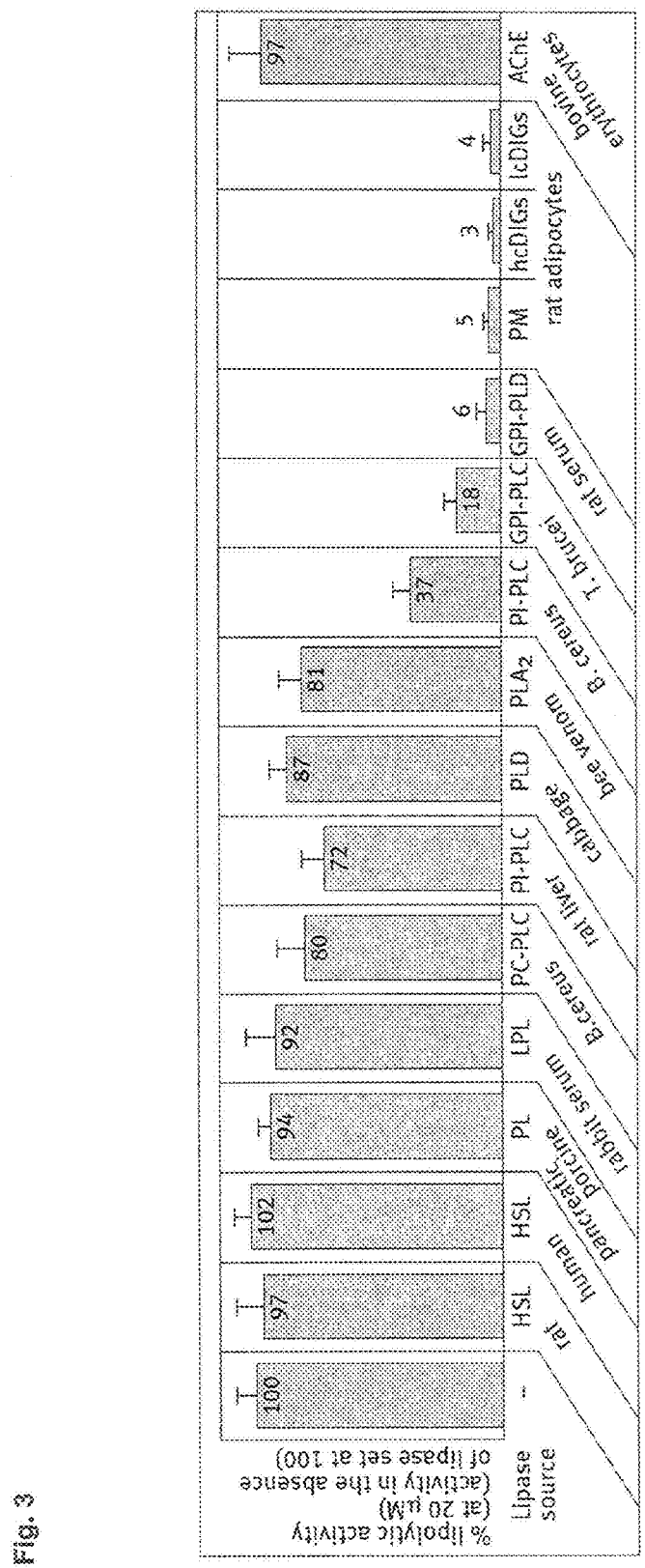
FIG. 3: Selectivity of GPI-2350. Various (partially) purified or recombinant lipases (HSL, hormone-sensitive lipase; PL, pancreatic lipase; LPL, lipoprotein lipase; PC-PLC, phosphatidylcholine-specific phospholipase C; PI-PLC, phosphatidylinositol-specific phospholipase C; PLD, phospholipase D; PLA$_2$, phospholipase A$_2$; GPI-PLC, glycosylphosphatidylinositol-specific PLC/D and AChE (acetylcholinesterase) of different origin as indicated as well as total plasma membranes (PM) and hc/lcDIGs from isolated rat adipocytes were assayed in the absence or presence of GPI-2350 (50 µM) according to typical assay protocols (see Materials and Methods). Means+SD of at least 3 independent incubations with measurements in duplicate each are given.
Figure 4:
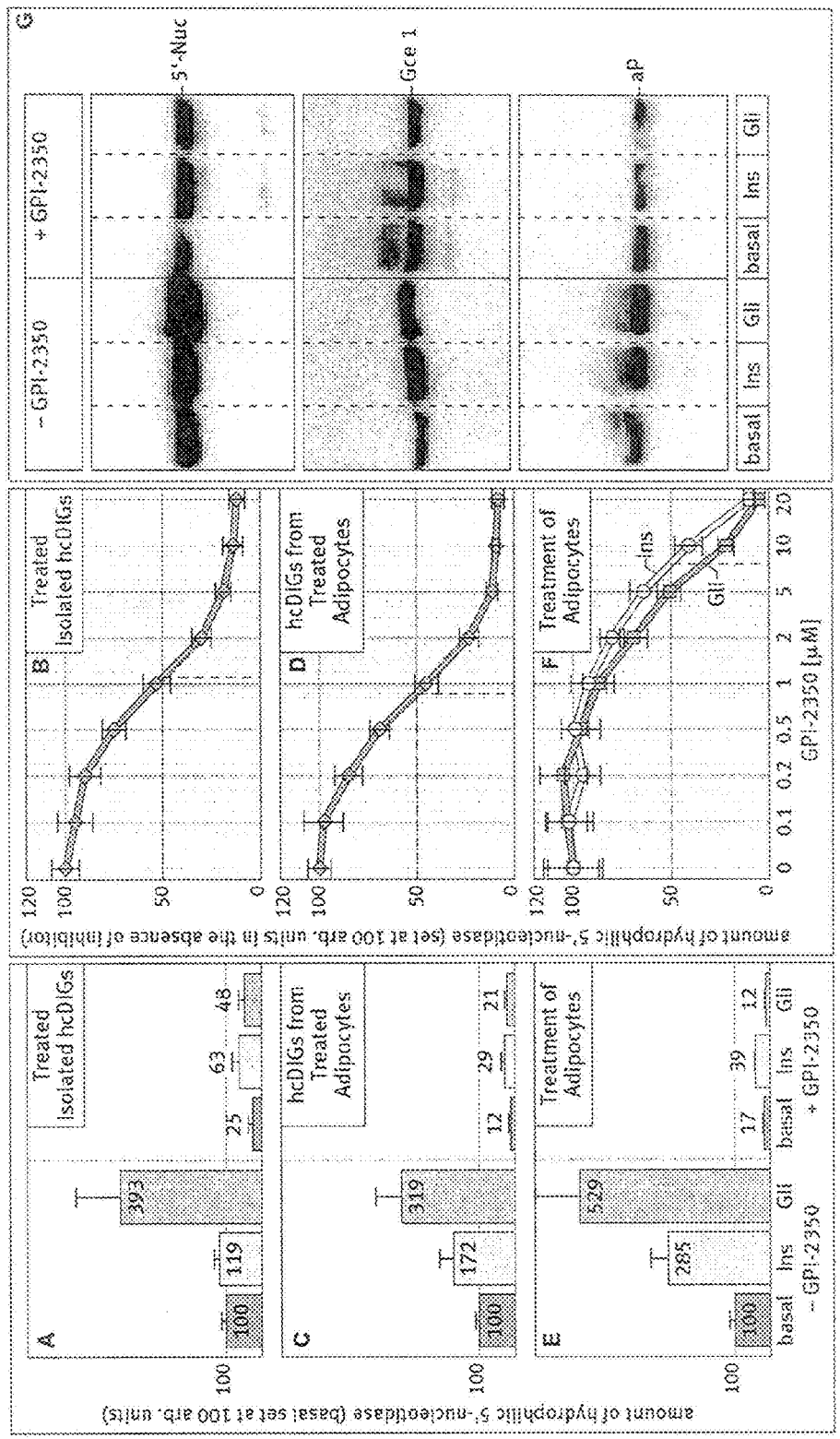
FIG. 4: Effect of GPI-2350 on cleavage of GPI-proteins by insulin-/glimepiride-induced GPI-PLC. Panels A and B. hcDIGs were prepared from untreated rat adipocytes and then incubated (5 min, 37° C.) in the absence or presence of GPI-2350 (panel A, 50 µM; panel B, increasing conc.) followed by treatment (120 min, 30° C.) without or with insulin (10 nM) or glimepiride (20 µM) as indicated. Panels C and D. Isolated rat adipocytes were incubated (15 min, 37° C.) in the absence or presence of insulin (10 nM) or glimepiride (20 µM) as indicated. hcDIGs were prepared and subsequently incubated (120 min, 30° C.) with GPI-2350 (panel C, 50 µM; panel D, increasing conc.). Panels E, F and G. Isolated rat adipocytes were incubated (5 min, 37° C.) in the absence or presence of GPI-2350 (panels E and G, 50 µM; panel F, increasing conc.) and then treated (90 min, 37° C.) without or with insulin (10 nM) or glimepiride (20 µM) as indicated. hcDIGs were prepared. Panels A-D. GPI-PLC activity in hcDIGs was measured with 5'-Nuc as exogenous substrate as conversion in its hydrophilic version. Panels E-G. Proteins recovered with the TX-114-depleted phase of hcDIGs were immunoblotted for hydrophilic 5'-Nuc and aP or analyzed for hydrophilic Gce1 by photoaffinity-labeling. Means+SE of 3 independent cell incubations with activity measurements and gel runs in duplicate (representative one shown) each are given.
Figure 5:
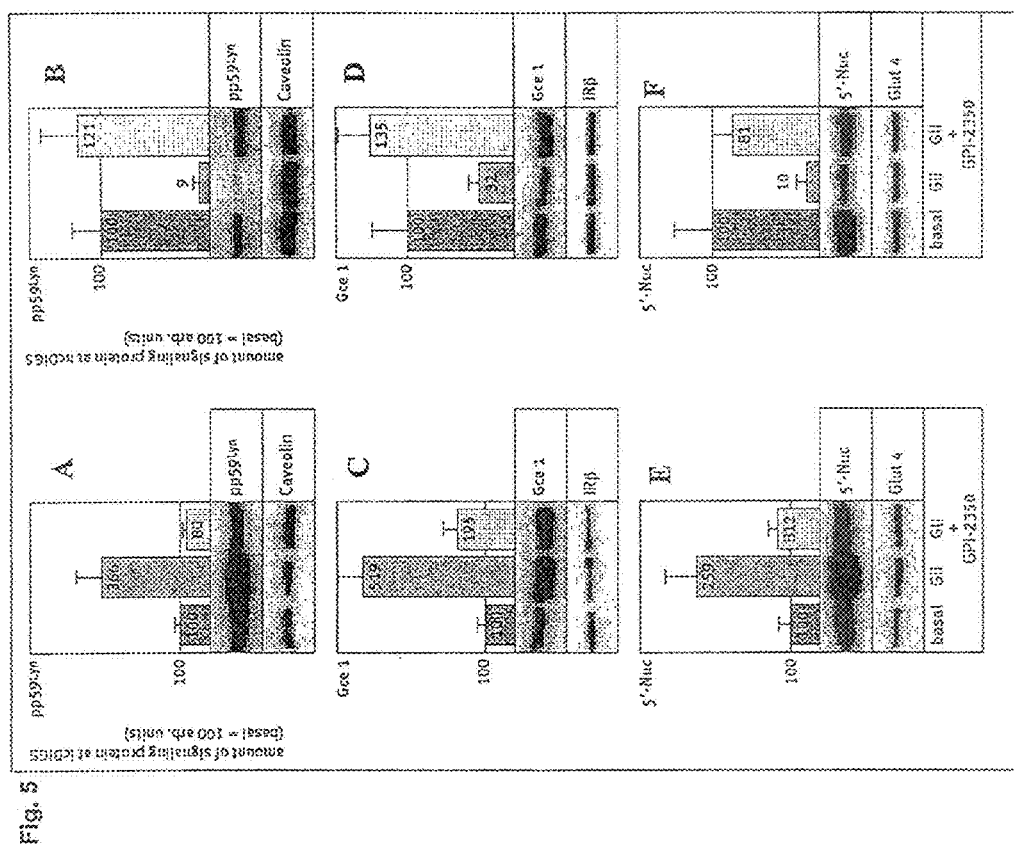
FIG. 5 A-F: Effect of GPI-2350 on the glimepiride-induced redistribution of signaling proteins within DIGs. Isolated rat adipocytes were treated (5 min, 37° C.) without or with GPI-2350 (50 µM final conc.) and then incubated (120 min, 37° C.) in the absence or presence of glimepiride (50 µM) as indicated. hcDIGs and lcDIGs were prepared and assayed for the presence of pp59$^{Lyn}$, 5'-Nuc, caveolin-1, insulin receptor beta-subunit (IRβ), glucose transporter 4 (Glut4) and Gce1 by immunoblotting and photoaffinity-labeling, respectively (see gel insets). The amount of pp59$^{Lyn}$, Gce1 and 5'-Nuc recovered with hc/lcDIGs is given relative to the control reaction (basal) in the absence of GPI-2350 (set at 100). Means+SD of at least 3 independent cell incubations with gel runs in duplicate (representative one shown) each are given.
Figure 6:
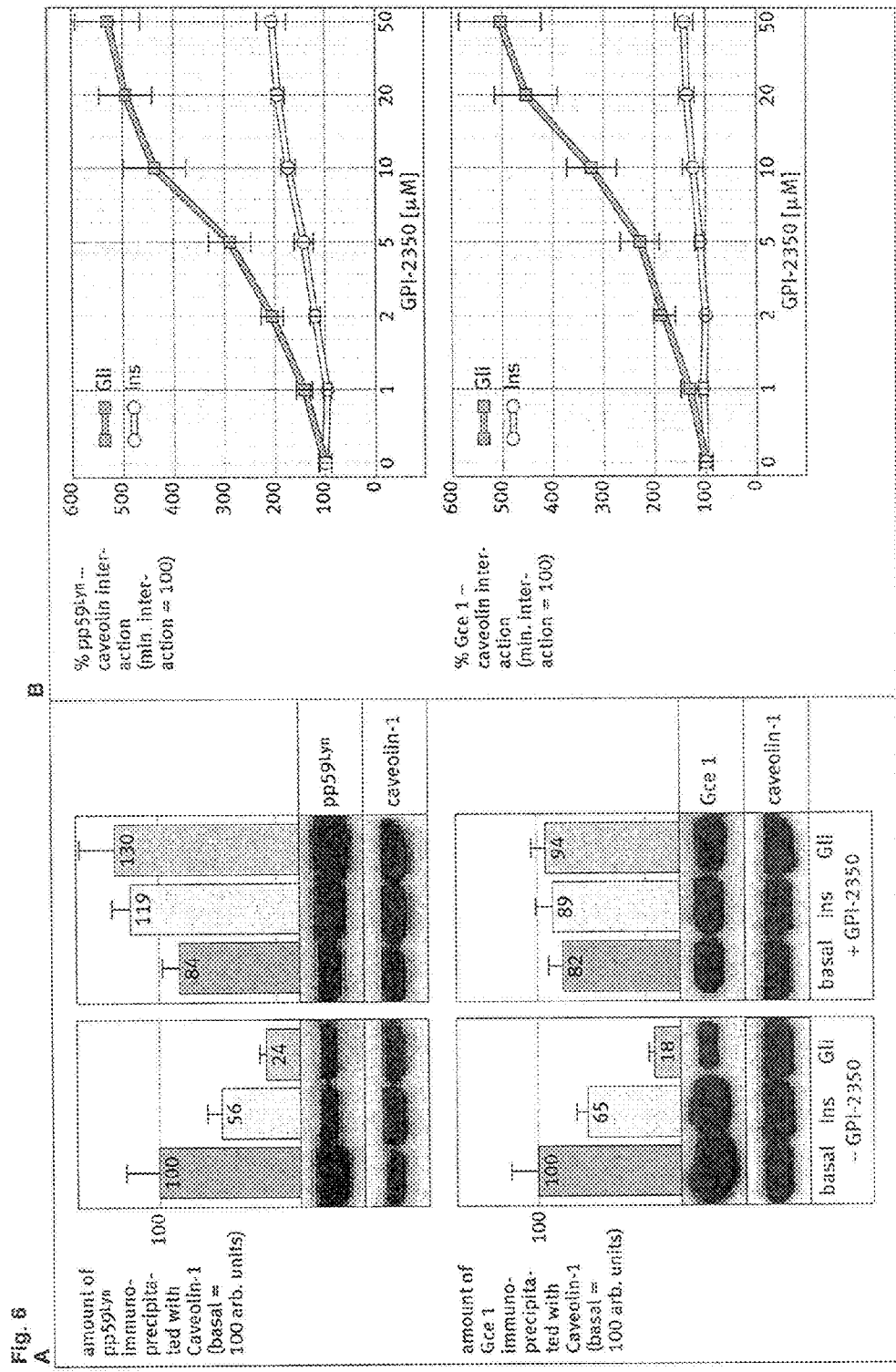
FIG. 6: Effect of GPI-2350 on the glimepiride/insulin-induced dissociation of signaling proteins from caveolin. Isolated rat adipocytes were treated (5 min, 37° C.) without or with GPI-2350 (left panels, 50 µM; right panels, increasing conc.) and then incubated (120 min, 37° C.) in the absence or presence of insulin (10 nM) or glimepiride (20 µM). hcDIGs were prepared from the adipocytes and then solubilized. Caveolin-1 immunoprecipitates prepared from the solubilized hcDIGs were assayed for the presence of pp59$^{Lyn}$ and Gce1 by immunoblotting and photoaffinity-labeling, respectively. The amount of pp59$^{Lyn}$ and Gce1 is given relative to the absence of GPI-2350 in the control reaction (Panels A, basal set at 100) or in the insulin- or glimepiride-stimulated state (Panels B, set at 100) after correction for the recovery of immunoprecipitated caveolin-1 by homologous immunoblotting (see gel insets). Means+SD of at least 4 independent cell incubations with gel runs in duplicate (representative one shown) each are given.
Figure 7:
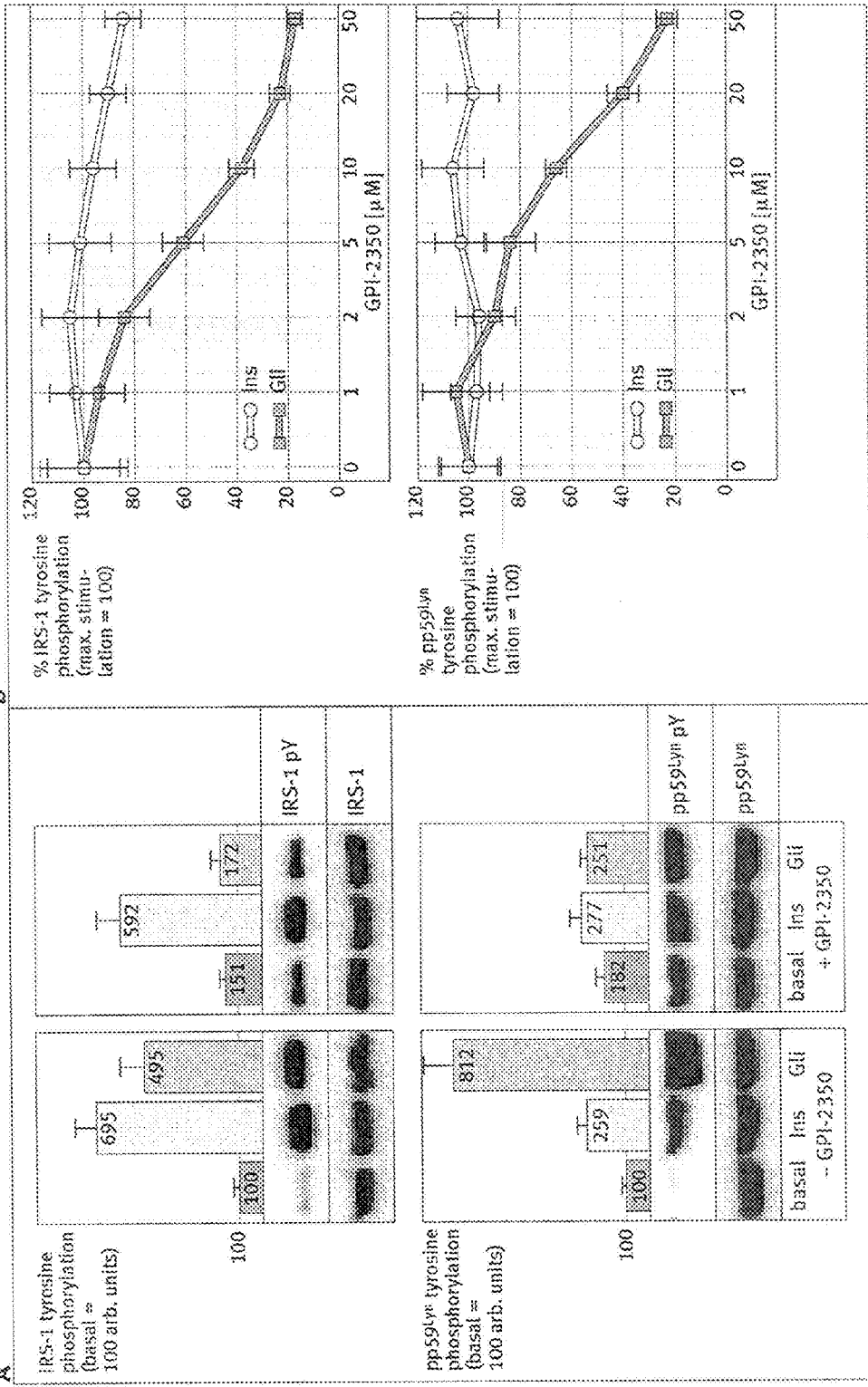
FIG. 7: Effect of GPI-2350 on the glimepiride/insulin-induced activation of signaling proteins. Isolated rat adipocytes were treated (5 min, 37° C.) without or with GPI-2350 (Panels A, 50 µM; Panels B, increasing conc.) and then incubated (120 min, 37° C.) in the absence or presence of insulin (10 nM) or glimepiride (20 μM). IRS-1 and pp59$^{Lyn}$ were immunoprecipitated from the defatted postnuclear infranatant (see Materials and Methods) and solubilized combined hc/lcDIGs, respectively, and then immunoblotted for phosphotyrosine. The amount of tyrosine-phosphorylated IRS-1 and pp59$^{Lyn}$ is given relative to the absence of GPI-2350 in the control reaction (Panels A, basal set at 100) or in the insulin- or glimepiride-stimulated state (Panels B, set at 100 in each case) after correction for the recovery of immunoprecipitated IRS-1 and pp59$^{Lyn}$ by homologous immunoblotting (see gel insets). Means+SD of at least 4 independent cell incubations with gel runs in duplicate (representative one shown) each are given.
Figure 8:
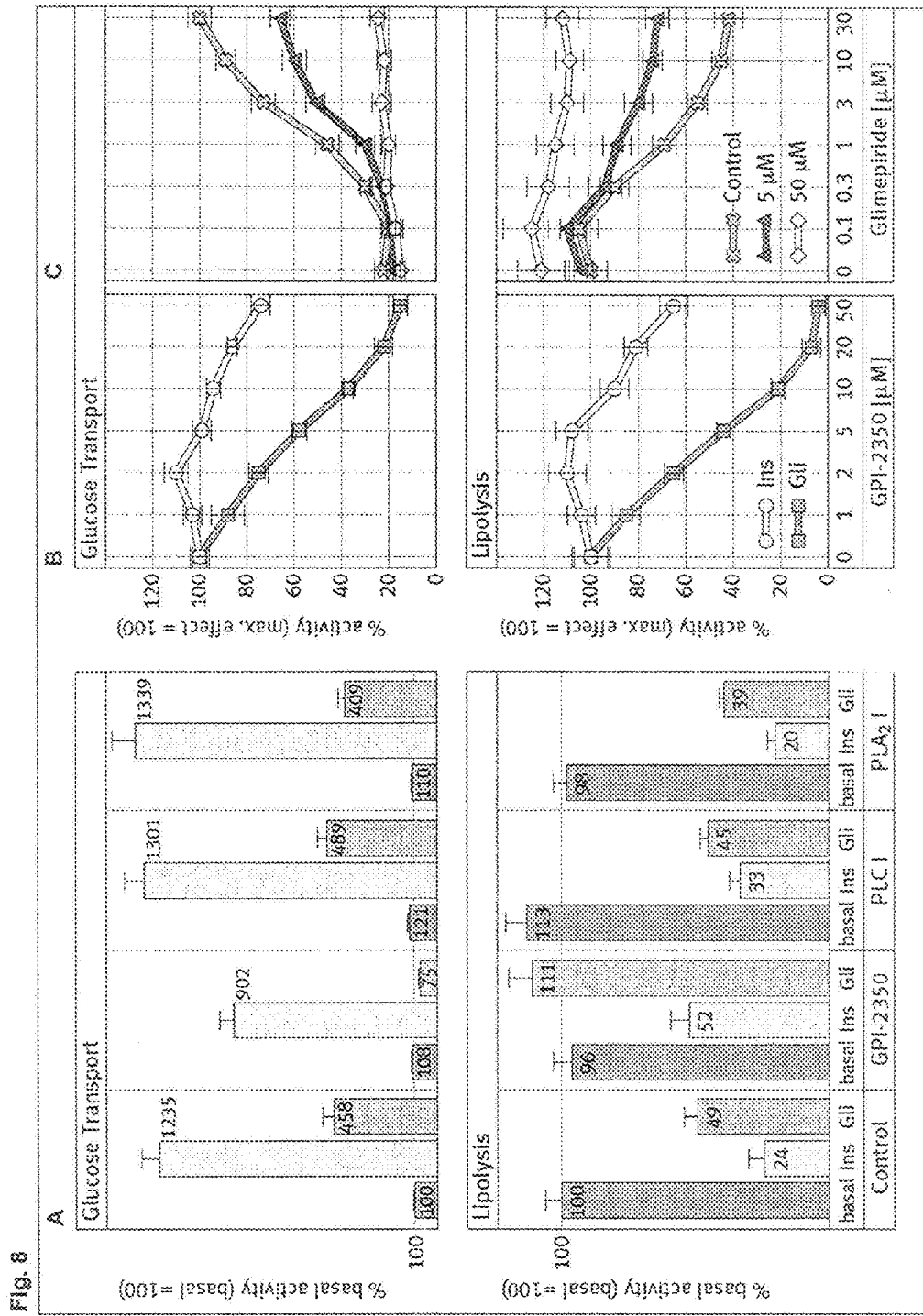
FIG. 8: Effect of GPI-2350 on the glimepiride/insulin-induced metabolic activity. Isolated rat adipocytes were treated (5 min, 37° C.) without or with GPI-2350 (Panel A, 50 μM; Panel B, increasing conc.; Panel C, 5 μM, 50 μM) and then incubated (15 min, 37° C.) in the absence or presence of insulin (Ins, 10 nM) or glimepiride (Gli, 20 μM or increasing conc.) as indicated. The adipocytes were then assayed for glucose transport and isoproterenol-induced lipolysis. The activity is given relative to the absence of GPI-2350 in the control reaction (Panels A, basal) or in the insulin- and glimepiride-stimulated state (Panels B and C, set at 100). Means+SD of at least 5 independent cell incubations with activity measurements in triplicate each are given.
Figure 9:
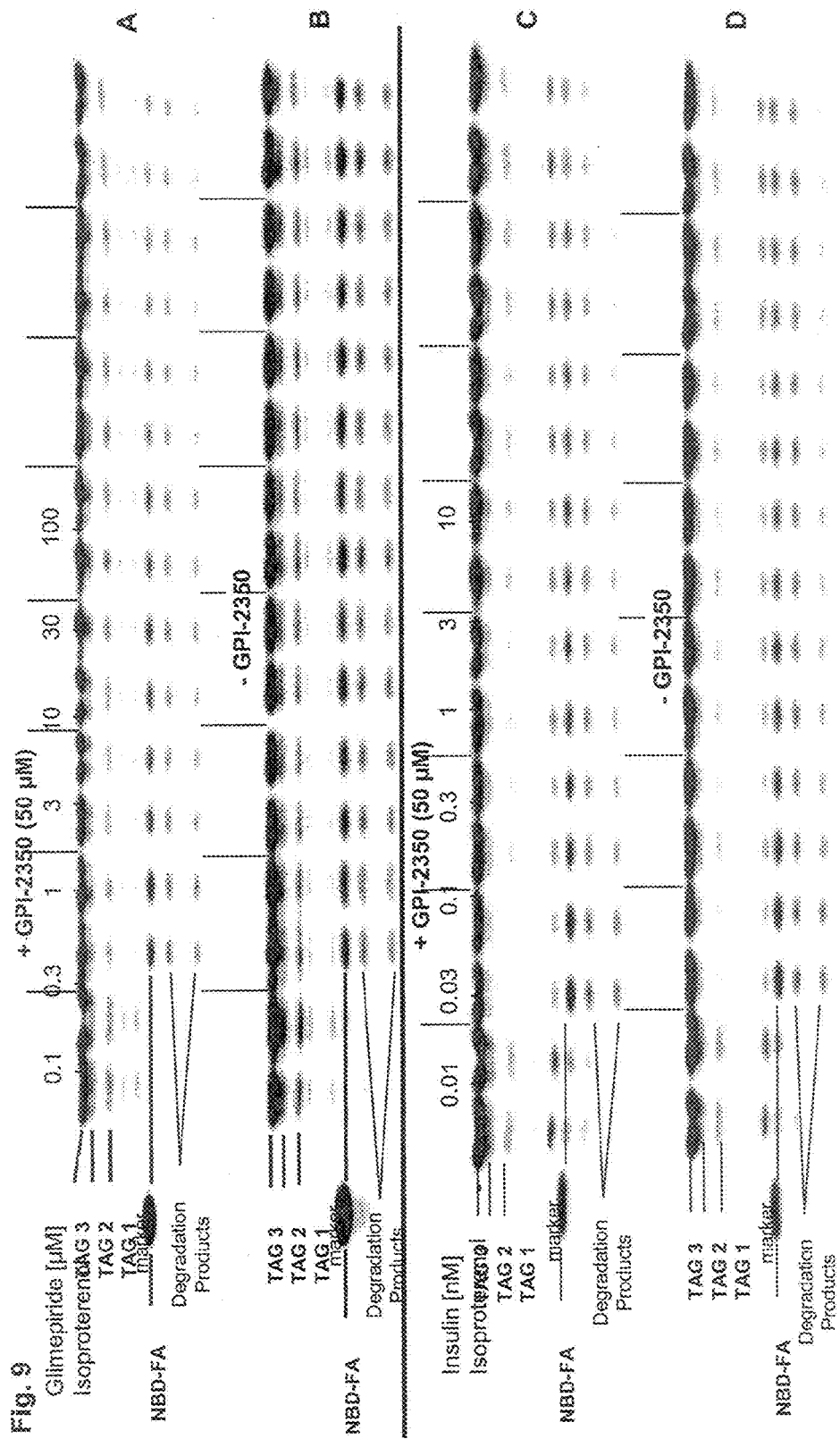
FIG. 9: Isolated rat adipocytes were labeled with 0.5 mM NBD-FA (60 min, 37° C.), washed and then incubated (5 min, 37° C.) in the absence (Panels B, D) or presence of GPI-2350 (50 μM; Panels A, C) prior to challenge with increasing concentrations of glimepiride (Panels A, B) or insulin (Panels C, D). After further incubation (120 min, 37° C.) without or with isoproterenol (1 μM) as indicated, total cell suspensions were extracted with chloroform/heptane/methanol/0.1 N HCl (3/3/2/1, by vol.). The organic phases were analyzed by thin layer chromatography (diethylether/petrolether/acetic acid 78/22/1, by vol.) and fluorescence imaging in parallel with NBD-FA as marker. A typical experiment with 2 independent labelings and incubations is shown repeated once with similar results. TAG, triacylglycerol.
Figure 10:
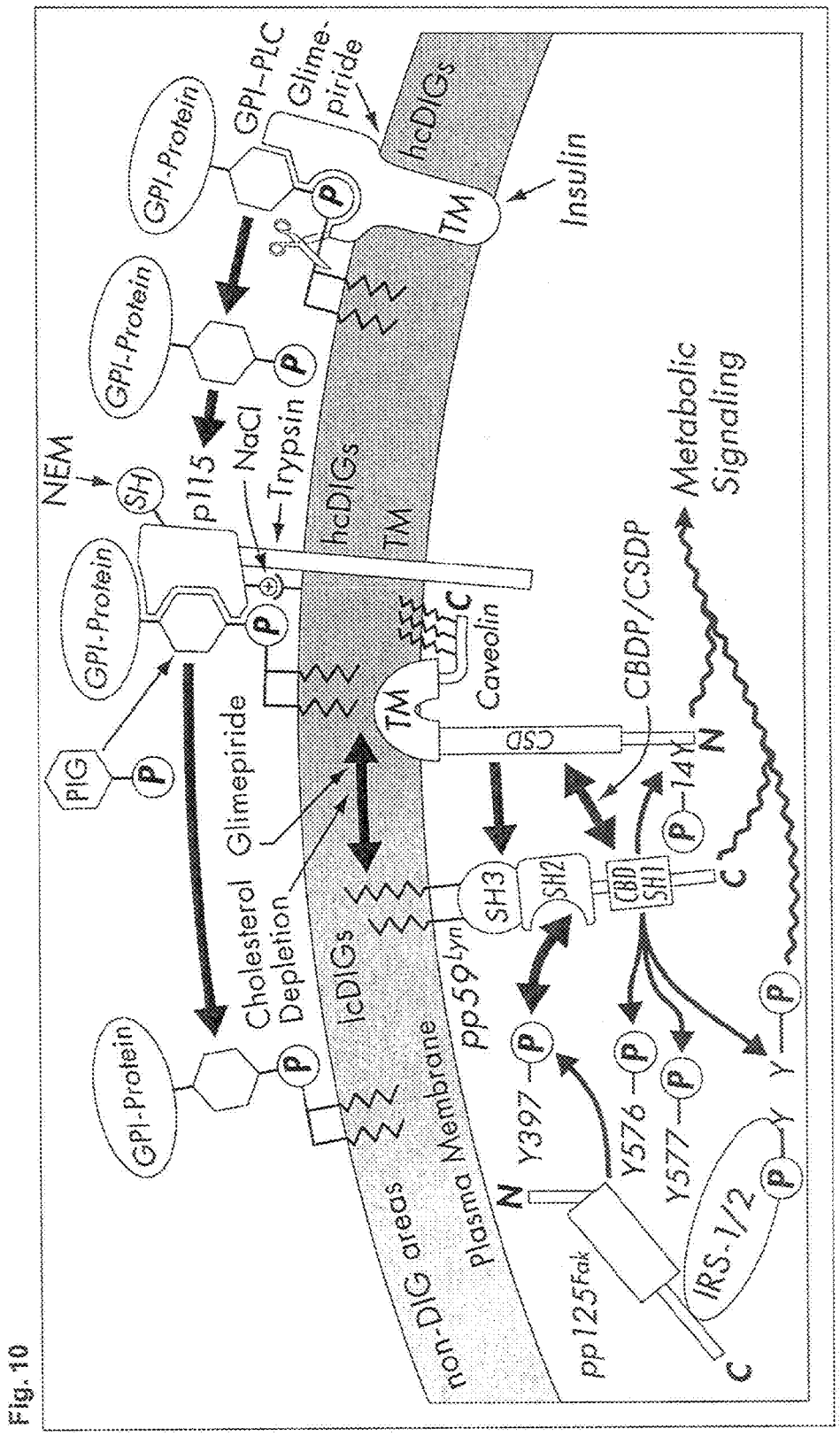
FIG. 10: Working model for the mechanism of redistribution of GPI-proteins between non-DIG areas, hcDIGs and lcDIGs of the rat adipocyte plasma membrane, its regulation by insulin, glimepiride and cholesterol depletion involving the GPI-PLC and the putative GPI-protein receptor, p115, and its coupling to downstream metabolic signaling via caveolin, pp125$^{Fak}$ and pp59$^{Lyn}$ to IRS-1. The topology, membrane orientation and type of anchorage at hcDIGs via transmembrane domains (TM) of the GPI-PLC and p115 are hypothetical. However, the active and binding sites, respectively, facing the extracellular leaflet of DIGs are strongly suggested on the basis of the demonstrated cell surface location of the majority of GPI-proteins. Caveolin is embedded in the cytoplasmic leaflet of hcDIGs by both a hook-like TM and triple palmitoylation at the carboxy-terminus, pp59$^{Lyn}$, by dual acylation at the amino-terminus.

We claim:

1. A method for identification of a chemical compound that modulates the activity of a mammalian Glycosyl-Phosphatidyl-Inositol specific Phospholipase C (GPI-PLC) which comprises the steps of:
a] incubating a mammalian cell with glimepiride to stimulate GPI-PLC activity;
b] preparing hcDIGs (high cholesterol detergent-insoluble glycolipid enriched raft domains) from said mammalian cells whereby between 65%-85% of the GPI-PLC activity of the incubated cell of step a] is retained and whereby stimulation of the GPI-PLC activity in the cell of step a] by glimepiride is preserved in the GPI-PLC of hcDIGs and is about 3-fold higher as compared to the GPI-PLC activity present in the hcDIGs of a non-stimulated mammalian cell, and the GPI-PLC activity is enriched in the hcDIGs as compared to the residual plasma membrane;
c] incubating the hcDIGs from step b] in the presence and absence of a test chemical compound;
d] determining the activity of the GPI-PLC by measuring the cleavage of endogenous GPI proteins through monitoring their amphiphilic-to-hydrophilic conversion from the hcDIGs of step c].

2. The method as claimed in claim 1 wherein the mammalian cell of step a] is a cell of a rodent, or a dog.

3. The method as claimed in claim 2, wherein the rodent is a mouse or a rat.

4. The method as claimed in claim 1, wherein the mammalian cell of step a] is a cell of a human.

5. The method as claimed in claim 1, wherein the cell is a pancreatic cell, a muscle cell, a liver cell, a kidney cell, a brain cell or an adipocyte.

6. A method for identification of a chemical compound that modulates the activity of glimepiride, comprising the steps of:
a] incubating a mammalian cell with a mix of glimepiride and a chemical compound;
b] preparing hcDIGs whereby between 65%-85% of GPI-PLC activity of the cell of step a] is retained in the hcDIGs in the absence of the chemical compound and whereby the stimulation of the GPI-PLC activity in the cell of step a] by glimepiride is preserved in the GPI-PLC of the hcDIGs and is about 3-fold higher as compared to the GPI-PLC activity present in hcDIGs of a non-stimulated mammalian cell, and the GPI-PLC activity is enriched in the hcDIGs as compared to the residual plasma membrane;
c] the activity of the GPI-PLC from the hcDIGs of step b] is determined by measuring the cleavage of endogenous GPI proteins through monitoring their amphiphilic-to-hydrophilic conversion;
d] incubating a mammalian cell with glimepiride;
e] preparing hcDIGs whereby between 65%-85% of GPI-PLC activity of the cell of step d] is retained in the hcDIGs and whereby the stimulation of the GPI-PLC activity in the cell of step d] by glimepiride is preserved in the GPI-PLC of the hcDIGs and is about 3-fold higher as compared to the GPI-PLC activity present in hcDIGs of a non-stimulated mammalian cell, and the GPI-PLC activity is enriched in the hcDIGs as compared to the residual plasma membrane;
f] the activity of the GPI-PLC from the hcDIGs of step d] is determined by measuring the cleavage of endogenous GPI proteins through monitoring their amphiphilic-to-hydrophilic conversion; and comparing the activity of GPI-PLC from steps c and f to determine if the chemical compound modulates the activity of glimepiride.

7. The method as claimed in claim 6, wherein the mammalian cell of steps a] and d] is a cell of a rodent or dog.

8. The method as claimed in claim 7, wherein the rodent is a mouse or a rat.

9. The method as claimed in claim 6, wherein the mammalian cell of steps a] and d] is a cell of a human.

10. The method as claimed in claim 6, wherein the cell is a pancreatic cell, a muscle cell, a liver cell, a kidney cell, a brain cell or an adipocyte.

11. The method as claimed in claim 6, wherein the mammalian cell is from a cell culture.

* * * * *